United States Patent
Meissner et al.

(10) Patent No.: US 7,410,977 B2
(45) Date of Patent: Aug. 12, 2008

(54) FLUORINATED 4-AZASTEROIDS AS ANDROGEN RECEPTOR MODULATORS

(75) Inventors: Robert S. Meissner, Schwenksville, PA (US); James J. Perkins, Churchville, PA (US)

(73) Assignee: Merck & Co., Inc., Rahway, NJ (US)

( * ) Notice: Subject to any disclaimer, the term of this patent is extended or adjusted under 35 U.S.C. 154(b) by 112 days.

(21) Appl. No.: 11/578,755

(22) PCT Filed: Apr. 22, 2005

(86) PCT No.: PCT/US2005/013775

§ 371 (c)(1), (2), (4) Date: Oct. 18, 2006

(87) PCT Pub. No.: WO2005/105091

PCT Pub. Date: Nov. 10, 2005

(65) Prior Publication Data

US 2007/0243266 A1    Oct. 18, 2007

(51) Int. Cl.
*A61K 31/473* (2006.01)
*C07D 221/18* (2006.01)

(52) U.S. Cl. .................................. 514/284; 546/77

(58) Field of Classification Search ................. 514/284; 546/77

See application file for complete search history.

(56) References Cited

U.S. PATENT DOCUMENTS 5,187,278 A    2/1993    King et al.

FOREIGN PATENT DOCUMENTS

WO    WO 03/077919 A1    9/2003

*Primary Examiner*—Charanjit S Aulakh
(74) *Attorney, Agent, or Firm*—Curtis C. Panzer; Patricia A. Shatynski; Valerie J. Camara

(57) ABSTRACT

Compounds of structural formula I are modulators of the androgen receptor (AR) in a tissue selective manner. These compounds are useful in the enhancement of weakened muscle tone and the treatment of conditions caused by androgen deficiency or which can be ameliorated by androgen administration, including osteoporosis, osteopenia, glucocorticoid-induced osteoporosis, periodontal disease, bone fracture, bone damage following bone reconstructive surgery, sarcopenia, frailty, aging skin, male hypogonadism, postmenopausal symptoms in women, atherosclerosis, hypercholesterolemia, hyperlipidemia, obesity, aplastic anemia and other hematopoietic disorders, inflammatory arthritis and joint repair, HIV-wasting, prostate cancer, benign prostatic hyperplasia (BPH), cancer cachexia, Alzheimer's disease, muscular dystrophies, cognitive decline, sexual dysfunction, sleep apnea, depression, premature ovarian failure, and autoimmune disease, alone or in combination with other active agents.

6 Claims, No Drawings

FLUORINATED 4-AZASTEROIDS AS ANDROGEN RECEPTOR MODULATORS

FIELD OF THE INVENTION

The present invention relates to fluorinated 4-azasteroid derivatives, their synthesis, and their use as androgen receptor modulators. More particularly, the compounds of the present invention are tissue-selective androgen receptor modulators (SARMs) and are thereby useful for the treatment of conditions caused by androgen deficiency or which can be ameliorated by androgen administration, such as osteoporosis, periodontal disease, bone fracture, frailty, and sarcopenia. Additionally, the SARMs of the present invention can be used to treat mental disorders associated with low testosterone, such as depression, sexual dysfunction, and cognitive decline. SARMs, being antagonists in specific tissues, are also useful in conditions where elevated androgen tone or activity causes symptoms, such as benign prostate hyperplasia and sleep apnea.

BACKGROUND OF THE INVENTION

The androgen receptor (AR) belongs to the superfamily of steroid/thyroid hormone nuclear receptors, whose other members include the estrogen receptor, the progesterone receptor, the glucocorticoid receptor, and the mineralocorticoid receptor. The AR is expressed in numerous tissues of the body and is the receptor through which the physiological as well as the pathophysiological effects of androgens, such as testosterone (T) and dihydrotestosterone (DHT), are mediated. Structurally, the AR is composed of three functional domains: the ligand binding domain (LBD), the DNA-binding domain, and amino-terminal domain. A compound that binds to the AR and mimics the effects of an endogenous AR ligand is referred to as an AR agonist, whereas a compound that inhibits the effects of an endogenous AR ligand is termed an AR antagonist.

Androgen ligand binding to the AR induces a ligand/receptor complex, which, after translocation into the nucleus of the cell, binds to regulatory DNA sequences (referred to as androgen response elements) within the promoter or enhancer regions of the target genes present in the nucleus. Other proteins termed cofactors are next recruited, which bind to the receptor leading to gene transcription.

Androgen therapy has been to treat a variety of male disorders such as reproductive disorders and primary or secondary male hypogonadism. Moreover, a number of natural or synthetic AR agonists have been investigated for the treatment of musculoskeletal disorders, such as bone disease, hematopoietic disorders, neuromuscular disease, rheumatological disease, wasting disease, and for hormone replacement therapy (HRT), such as female androgen deficiency. In addition, AR antagonists, such as flutamide and bicalutamide, are used to treat prostate cancer. It would therefore be useful to have available compounds that can activate ("agonize") the function of the AR in a tissue-selective manner that would produce the desired osteo- and myoanabolic effects of androgens without the negative androgenic properties, such as virilization and repression of high density lipoprotein cholesterol (HDL).

The beneficial effects of androgens on bone in postmenopausal osteoporosis were documented in recent studies using combined testosterone and estrogen administration [Hofbauer, et al., *Eur. J. Endocrinol.* 140: 271-286 (1999)]. In a large 2-year, double-blind comparison study, oral conjugated estrogen (CEE) and methyltestosterone combinations were demonstrated to be effective in promoting accrual of bone mass in the spine and hip, while conjugated estrogen therapy alone prevented bone loss [*J. Reprod. Med.*, 44: 1012-1020 (1999)].

Additionally, there is evidence that hot flashes decrease in women treated with CEE and methyltestosterone; however, 30% of the treated women suffered from significant increases in acne and facial hair, a complication of all current androgen pharmacotherapies [Watts, et al., *Obstet. Gynecol.*, 85: 529-537 (1995)]. It was also found that the addition of methyltestosterone to CEE decreased HDL levels, as seen in other studies. Thus, the virilizing potential and effects on lipid profile of current androgen therapies provide a rationale for developing tissue-selective androgen receptor agonists.

Androgens play an important role in bone metabolism in men [Anderson, et al., "Androgen supplementation in eugonadal men with osteoporosis—effects of six months of treatment on bone mineral density and cardiovascular risk factors," *Bone*, 18: 171-177 (1996)]. Even in eugonadal men with osteoporosis, the therapeutic response to testosterone treatment reveals that androgens exert important osteoanabolic effects. Mean lumbar BMD increased from 0.799 gm/cm2 to 0.839 g/cm2, in 5 to 6 months in response to 250 mg of testosterone ester administered intramuscularly. SARMs can thus be used to treat osteoporosis in men.

Androgen deficiency occurs in men with stage D prostate cancer (metastatic) who undergo androgen deprivation therapy (ADT). Endocrine orchiectomy is achieved by long acting GnRH agonists, while androgen receptor blockade is implemented with AR antagonists. In response to hormonal deprivation, these men suffered from hot flushes, significant bone loss, weakness, and fatigue. In a pilot study of men with stage D prostate cancer, osteopenia (50% vs. 38%) and osteoporosis (38% vs. 25%) were more common in men who had undergone ADT for greater than one year than the patients who did not undergo ADT [Wei, et al., *Urology*, 54: 607-611 (1999)]. Lumbar spine BMD was significantly lower in men who had undergone ADT. Thus tissue selective AR antagonists in the prostate that lack antagonistic action in bone and muscle can be useful agents for the treatment of prostate cancer, either alone or as an adjunct to traditional ADT [See also A. Stoch, et al., *J. Clin. Endocrin. Metab.*, 86: 2787-2791 (2001)].

Tissue-selective AR antagonists can also treat polycystic ovarian syndrome in postmenopausal women. See C. A. Eagleson, et al., "Polycystic ovarian syndrome: evidence that flutamide restores sensitivity of the gonadotropin-releasing hormone pulse generator to inhibition by estradiol and progesterone," *J. Clin. Endocrinol. Metab.*, 85: 4047-4052 (2000).

SARMs can also treat certain hematopoietic disorders as androgens stimulate renal hypertrophy and erythropoietin (EPO) production. Prior to the introduction of recombinant human EPO, androgens were employed to treat anemia caused by chronic renal failure. In addition, androgens increase serum EPO levels in anemic patients with non-severe aplastic anemia and myelodysplastic syndromes. Treatment for anemia will require selective action such as can be provided by SARMs.

SARMs can also have clinical value as an adjunct to the treatment of obesity. This approach to lowering body fat is supported by published observations that androgen administration reduced subcutaneous and visceral fat in obese patients [J. C. Lovejoy, et al., "Oral anabolic steroid treatment, but not parenteral androgen treatment, decreases abdominal fat in obese, older men," *Int. J. Obesity*, 19: 614-624 (1995)], [J. C. Lovejoy, et al., "Exogenous Androgens Influence Body Composition and Regional Body Fat Distribution in Obese Postmenopausal Women—A Clinical Research Center Study," *J. Clin. Endocrinol. Metab.*, 81: 2198-2203 (1996)]. Therefore, SARMs devoid of unwanted androgenic effects can be beneficial in the treatment of obesity.

Androgen receptor agonists can also have therapeutic value against neurodegenerative diseases such as Alzheimer's disease (AD). The ability of androgens to induce neuroprotection through the androgen receptor was reported by J. Hammond, et al., "Testosterone-mediated neuroprotection through the androgen receptor in human primary neurons," *J. Neurochem.*, 77: 1319-1326 (2001). Gouras et al. reported that testosterone reduces secretion of Alzheimer's β-amyloid peptides and can therefore be used in the treatment of AD [(*Proc. Nat. Acad. Sci.*, 97: 1202-1205 (2000)]. A mechanism via inhibition of hyperphosphorylation of proteins implicated in the progression AD has also been described [S. Papasozomenos, "Testosterone prevents the heat shock-induced overactivation of glycogen synthase kinase-3, but not of cyclin-dependent kinase 5 and c-Jun NH2-terminal kinase and concomitantly abolishes hyperphosphorylation of τ: Implications for Alzheimer's disease," *Proc. Nat. Acad. Sci.*, 99: 1140-1145 (2002)].

Androgen receptor agonists can also have a beneficial effect on muscle tone and strength. Recent studies have demonstrated that "physiologic androgen replacement in healthy, hypogonadal men is associated with significant gains in fat-free mass, muscle size and maximal voluntary strength," [S. Bhasin, et al., *J. Endocrin.*, 170: 27-38 (2001)].

Androgen receptor modulators can be useful in treating decreased libido in both men and women. Androgen deficiency in men is related to diminished libido. S. Howell et al., *Br. J. Cancer*, 82: 158-161. Low androgen levels contribute to the decline in sexual interest in many women during their later reproductive years. S. Davis, *J. Clin. Endocrinol. Metab.*, 84: 1886-1891 (1999). In one study, circulating free testosterone was positively correlated with sexual desire. Id. In another study, women with primary or secondary adrenal insufficiency were provided physiological DHEA replacement (50 mg/day). Compared with women taking placebo, DHEA-administered women showed an increase in the frequency of sexual thoughts, interest, and satisfaction. W. Arlt, et al., *N Engl. J. Med.* 341:1013-1020 (1999), see also, K. Miller, *J. Clin. Endocrinol. Metab.*, 86: 2395-2401 (2001).

Additionally, androgen receptor modulators may also be useful in treating cognitive impairment. In a recent study, high-dose oral estrogen either alone or in combination with high-dose oral methyltestosterone was given to postmenopausal women for a four-month period. Cognitive tests were administered before and after the four-month hormone treatment. The investigation found that women receiving a combination of estrogen (1.25 mg) and methyltestosterone (2.50 mg) maintained a steady level of performance on the Building Memory task, but the women receiving estrogen (1.25 mg) alone exhibited decreased performance. A. Wisniewski, *Horm. Res.* 58:150-155 (2002).

International application WO03/077919 discloses fluorinated 4-azasteroid derivatives, their synthesis, and their use as androgen receptor modulators.

SUMMARY OF THE INVENTION

The present invention relates to compounds of structural formula I:

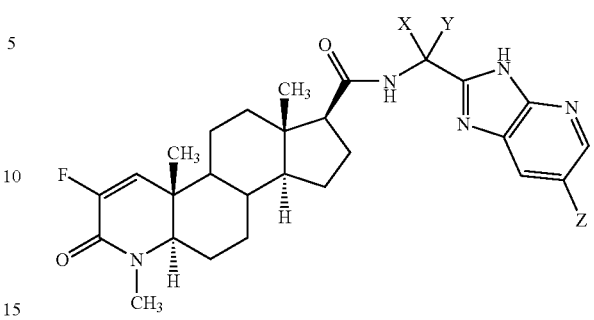

or a pharmaceutically acceptable salt or stereoisomer thereof, their uses and pharmaceutical compostions.

These compounds are effective as androgen receptor agonists and are particularly effective as SARMs. They are therefore useful for the treatment of conditions caused by androgen deficiency or which can be ameliorated by androgen administration.

The present invention also relates to pharmaceutical compositions comprising the compounds of the present invention and a pharmaceutically acceptable carrier.

In this invention, we have identified compounds that function as SARMs using a series of in vitro cell-assays that profile ligand mediated activation of AR, such as (i) N—C interaction, (ii) transcriptional repression, and (iii) transcriptional activation. SARM compounds in this invention, identified with the methods listed above, exhibit tissue selective AR agonism in vivo, i.e. agonism in bone (stimulation of bone formation in a rodent model of osteoporosis) and antagonism in prostate (minimal effects on prostate growth in castrated rodents and antagonism of prostate growth induced by AR agonists).

The compounds of the present invention identified as SARMs are useful to treat diseases or conditions caused by androgen deficiency which can be ameliorated by androgen administration. Such compounds are ideal for the treatment of osteoporosis in women and men as a monotherapy or in combination with inhibitors of bone resorption, such as bisphosphonates, estrogens, SERMs, cathepsin K inhibitors, αvβ3 integrin receptor antagonists, calcitonin, and proton pump inhibitors. They can also be used with agents that stimulate bone formation, such as parathyroid hormone or analogs thereof. The SARM compounds of the present invention can also be employed for treatment of prostate disease, such as prostate cancer and benign prostatic hyperplasia (BPH). Moreover, compounds of this invention exhibit minimal effects on skin (acne and facial hair growth) and can be useful for treatment of hirsutism. Additionally, compounds of this invention can stimulate muscle growth and can be useful for treatment of sarcopenia and frailty. They can be employed to reduce visceral fat in the treatment of obesity. Moreover, compounds of this invention can exhibit androgen agonism in the central nervous system and can be useful to treat vasomotor symptoms (hot flush) and to increase energy and libido. They can be used in the treatment of Alzheimer's disease.

The compounds of the present invention can also be used in the treatment of prostate cancer, either alone or as an adjunct to GnRH agonist/antagonist therapy, for their ability to restore bone, or as a replacement for antiandrogen therapy because of their ability to antagonize androgen in the prostate, and minimize bone depletion. Further, the compounds of the present invention can be used for their ability to restore bone in the treatment of pancreatic cancer as an adjunct to treatment with antiandrogen, or as monotherapy for their antiandrogenic properties, offering the advantage over traditional antiandrogens of being bone-sparing. Additionally, compounds of this invention can increase the number of blood cells, such as red blood cells and platelets, and can be useful for the treatment of hematopoietic disorders, such as aplastic anemia. Thus, considering their tissue selective androgen receptor agonism listed above, the compounds of this invention are ideal for hormone replacement therapy in hypogonadic (androgen deficient) men.

DETAILED DESCRIPTION OF THE INVENTION

The present invention relates to compounds that are useful as androgen receptor modulators, in particular, as selective androgen receptor modulators (SARMs). Compounds of the present invention are described by structural formula I:

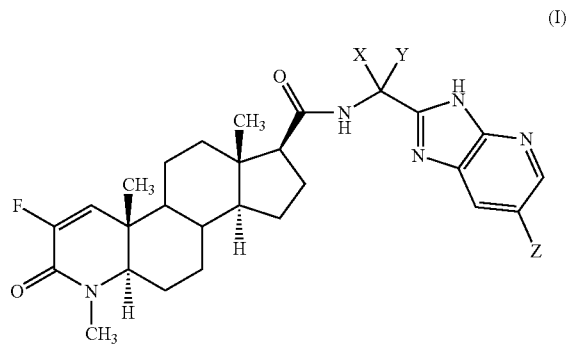

(I)

a pharmaceutically acceptable salt or a stereoisomer thereof, wherein:

X and Y are each independently chosen from hydrogen, halogen, hydroxy, and $C_{1-3}$ alkyl, wherein said alkyl is optionally substituted with one to seven fluorine atoms, provided that when X is methyl than Y is other than methyl; or X and Y, together with the carbon atom to which they are attached, can optionally form a $C_{3-6}$ cycloalkyl group; and Z is chosen from hydrogen, carbonyl($C_{1-3}$ alkyl), hydroxy, $C_{1-4}$ alkoxy, halogen, hydroxymethyl, ($C_{0-6}$ alkyl)$_2$-amino, and $C_{1-3}$ alkyl, wherein said alkoxy and alkyl are each optionally substituted with one to seven fluorine atoms; and provided that when X is hydrogen, Y is other than hydrogen.

Illustrative examples of compounds of the present invention are the following:

N-[1(R)-(3H-imidazo[4,5-b]pyridin-2-yl)ethyl]-2-fluoro-4-methyl-3-oxo-4-aza-5α-androst-1-en-17β-carboxamide;

N-[1(S)-(3H-imidazo[4,5-b]pyridin-2-yl)ethyl]-2-fluoro-4-methyl-3-oxo-4-aza-5α-androst-1-en-17β-carboxamide;

N-[1-(methyl)-1-(3H-imidazo[4,5-b]pyridin-2-yl)ethyl]-2-fluoro-4-methyl-3-oxo-4-aza-5α-androst-1-en-17β-carboxamide;

N-[1-(3H-imidazo[4,5-b]pyridin-2-yl)cyclopropyl]-2-fluoro-4-methyl-3-oxo-4-aza-5α-androst-1-en-17β-carboxamide;

N-[1(R)-(3H-imidazo[4,5-b]-(5-bromopyridin)-2-yl)ethyl]-2-fluoro-4-methyl-3-oxo-4-aza-5α-androst-1-en-17β-carboxamide; and pharmaceutically acceptable salts and stereoisomers thereof.

Unexpectedly, the compounds of the present invention exhibit favorable pharmaceutical activity in the appropriate combination of in vitro and in vivo assays. The presently exemplified compounds were subject to the following in vitro cell-assays that profile ligand mediated activation of AR: (i) the binding to endogenously expressed human AR in cell lysates, (ii) the transactivation of a model promoter via endogenous human AR in tissue culture, and (iii) the interaction between N-terminus and C-terminus domains of the AR in both the antagonist and agonist mode. These tests are designed to measure a compound's partial agonist activity.

In each of the above-mentioned in vitro assays, the compounds of the present invention showed an appropriate level of partial agonism activity. For example in the hydroxylapatite-based radioligand displacement assay of compound affinity for endogenously expressed AR, the exemplified compounds display a binding activity of 0.050 micromolar or less. This is a 20 fold increase in the normally acceptable $IC_{50}$ value of 1.0 micromolar or less. The affinity for a particular receptor is typically related to the potency of a given compound as a drug. So a compound with an $IC_{50}$ value of 0.050 micromolar can be 20 times more potent than a compound having an $IC_{50}$ value of 1.0 micromolar.

Coupled with the favorable in vitro profiles, the SARM compounds of this invention can also exhibit tissue selective AR agonism in vivo, i.e. agonism in bone (stimulation of bone formation in a rodent model of osteoporosis) and minimal effects on prostate growth in castrated rodents. The combination of appropriate level of activities in each of these assays distinguish the compounds of the present invention.

The compounds of the present invention can have asymmetric centers, chiral axes, and chiral planes (as described in: E. L. Eliel and S. H. Wilen, *Stereochemistry of Carbon Compounds*, John Wiley & Sons, New York, 1994, pages 1119-1190), and occur as racemates, racemic mixtures, and as individual diastereomers, with all possible isomers and mixtures thereof, including optical isomers, being included in the present invention.

In addition, the compounds disclosed herein can exist as tautomers and both tautomeric forms are intended to be encompassed by the scope of the invention, even though only one tautomeric structure is depicted. For example, any claim to compound A below is understood to include tautomeric structure B, and vice versa, as well as mixtures thereof. The term ⁓ represents the remainder of the 4-azasteroid derivatives of the present invention.

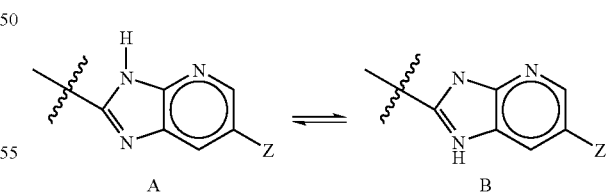

A  B

The term "alkyl" shall mean straight or branched chain alkanes of one to ten total carbon atoms, or any number within this range (i.e., methyl, ethyl, 1-propyl, 2-propyl, n-butyl, s-butyl, t-butyl, etc.). The term "$C_0$ alkyl" (as in "$C_{0-8}$ alkylaryl") shall refer to the absence of an alkyl group.

"Cycloalkyl" as used herein is intended to include non-aromatic cyclic hydrocarbon groups, having the specified number of carbon atoms, which may or may not be bridged or structurally constrained. Examples of such cycloalkyls include, but are not limited to, cyclopropyl, cyclobutyl, cyclopentyl, cyclohexyl, adamantyl, cyclooctyl, and the like. As used herein, examples of "$C_{3-6}$ cycloalkyl" can include, but are not limited to:

"Alkoxy" represents either a cyclic or non-cyclic alkyl group of indicated number of carbon atoms attached through an oxygen bridge. "Alkoxy" therefore encompasses the definitions of alkyl and cycloalkyl above.

"Perfluoroalkyl" represents alkyl chains of up to 10 carbon atoms having exhaustive substitution of their corresponding hydrogens with fluorine atoms.

As appreciated by those of skill in the art, "halo" or "halogen" as used herein is intended to include chloro, fluoro, bromo and iodo.

The term "oxy" means an oxygen (O) atom. The term "thio" means a sulfur (S) atom. The term "oxo" means "=O". The term "carbonyl" means "C=O."

The term "substituted" shall be deemed to include multiple degrees of substitution by a named substituent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

When any variable (e.g., $R^5$, $R^6$, etc.) occurs more than one time in any substituent or in formula I, its definition in each occurrence is independent of its definition at every other occurrence. Also, combinations of substituents and/or variables are permissible only if such combinations result in stable compounds.

Under standard nomenclature used throughout this disclosure, the terminal portion of the designated side chain is described first, followed by the adjacent functionality toward the point of attachment. For example, a $C_{1-5}$ alkylcarbonylamino $C_{1-6}$ alkyl substituent is equivalent to

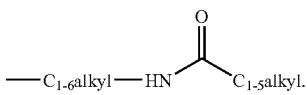

In choosing compounds of the present invention, one of ordinary skill in the art will recognize that the various substituents, i.e. X, Y, Z, etc., are to be chosen in conformity with well-known principles of chemical structure connectivity.

Lines drawn into the ring systems from substituents indicate that the indicated bond can be attached to any of the substitutable ring atoms. If the ring system is polycyclic, it is intended that the bond be attached to any of the suitable carbon atoms on the proximal ring only.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups can be on the same carbon or on different carbons, so long as a stable structure results. The phrase "optionally substituted with one or more substituents" should be taken to be equivalent to the phrase "optionally substituted with at least one substituent" and in such cases one embodiment will have from zero to three substituents.

In one embodiment of the invention, X and Y are each independently chosen from hydrogen, halogen, and $C_{1-3}$ alkyl, wherein said alkyl is optionally substituted with one to seven fluorine atoms. X and Y are each independently chosen from hydrogen, halogen, hydroxy, and $C_{1-3}$ alkyl, wherein said alkyl is optionally substituted with one to seven fluorine atoms, provided that when X is methyl than Y is other than methyl; or In yet another embodiment of the invention, X and Y, together with the carbon atom to which they are attached, can optionally form a $C_{3-6}$ cycloalkyl group, such as for example a cyclopropyl or cyclopentyl group. In a variant of this embodiment, X and Y together with the carbon atom to which they are attached form a cyclopropyl group.

In one embodiment of the invention, Z is chosen from hydrogen, carbonyl($C_{1-3}$ alkyl), hydroxy, $C_{1-4}$ alkoxy, and $C_{1-3}$ alkyl, wherein said alkoxy and alkyl are each optionally substituted with one to seven fluorine atoms. In one embodiment of the invention, Z is chosen from hydrogen, halogen, ($C_{0-6}$ alkyl)$_2$amino $C_{0-6}$alkyl, and $C_{1-3}$ alkyl, wherein said alkyl is optionally substituted with one to seven fluorine atoms. In a variant of this embodiment, Z is chosen from hydrogen, halogen, $CF_3$, and $C_{1-3}$ alkyl. In another variant, Z is bromine.

In one embodiment of the invention, the compounds are chosen from N-[1(R)-(3H-imidazo[4,5-b]pyridin-2-yl)ethyl]-2-fluoro-4-methyl-3-oxo-4-aza-5α-androst-1-en-17β-carboxamide; N-[1(S)-(3H-imidazo[4,5-b]pyridin-2-yl)ethyl]-2-fluoro-4-methyl-3-oxo-4-aza-5α-androst-1-en-17β-carboxamide; and pharmaceutically acceptable salts and stereoisomers thereof. In one variant, the compound is N-[1(R)-(3H-imidazo[4,5-b]pyridin-2-yl)ethyl]-2-fluoro-4-methyl-3-oxo-4-aza-5α-androst-1-en-17β-carboxamide and pharmaceutically acceptable salts and stereoisomers thereof.

In another embodiment of the invention, the compounds are chosen from: N-[1-(methyl)-1-(3H-imidazo[4,5-b]pyridin-2-yl)ethyl]-2-fluoro-4-methyl-3-oxo-4-aza-5α-androst-1-en-17β-carboxamide; N-[1-(3H-imidazo[4,5-b]pyridin-2-yl)cyclopropyl]-2-fluoro-4-methyl-3-oxo-4-aza-5α-androst-1-en-17β-carboxamide; N-[1(R)-(3H-imidazo[4,5-b]-(5-bromopyridin)-2-yl)ethyl]-2-fluoro-4-methyl-3-oxo-4-aza-5α-androst-1-en-17β-carboxamide; and pharmaceutically acceptable salts and stereoisomers thereof. In a variant of this embodiment the compound is N-[1-(3H-imidazo[4,5-b]pyridin-2-yl)cyclopropyl]-2-fluoro-4-methyl-3-oxo-4-aza-5α-androst-1-en-17β-carboxamide and pharmaceutically acceptable salts thereof. In yet another variant, the compound is chosen from: N-[1-(methyl)-1-(3H-imidazo[4,5-b]pyridin-2-yl)ethyl]-2-fluoro-4-methyl-3-oxo-4-aza-5α-androst-1-en-17β-carboxamide; N-[1(R)-(3H-imidazo[4,5-b]-(5-bromopyridin)-2-yl)ethyl]-2-fluoro-4-methyl-3-oxo-4-aza-5α-androst-1-en-17β-carboxamide; and pharmaceutically acceptable salts and stereoisomers thereof.

Compounds of the present invention have been found to be tissue-selective modulators of the androgen receptor (SARMs). In one aspect, compounds of the present invention can be useful to activate the function of the androgen receptor in a mammal, and in particular to activate the function of the androgen receptor in bone and/or muscle tissue and block or inhibit ("antagonize") the function of the androgen receptor in the prostate of a male individual or in the uterus of a female individual.

A further aspect of the present invention is the use of compounds of formula I to attenuate or block the function of the androgen receptor in the prostate of a male individual or in the uterus of a female individual induced by AR agonists, but not in hair-growing skin or vocal cords, and activate the function of the androgen receptor in bone and/or muscle tissue, but not in organs which control blood lipid levels (e.g. liver).

Representative compounds of the present invention typically display submicromolar binding affinity for the androgen receptor. Compounds of this invention are therefore useful in treating mammals suffering from disorders related to androgen receptor function. Therapeutically effective amounts of the compound, including the pharmaceutically acceptable salts thereof, are administered to the mammal, to treat disorders related to androgen receptor function, such as, androgen deficiency, disorders which can be ameliorated by androgen replacement, or which can be improved by androgen replacement, including: enhancement of weakened muscle tone, osteoporosis, osteopenia, glucocorticoid-induced osteoporosis, periodontal disease, bone fracture (for example, vertebral and non-vertebral fractures), bone damage following bone reconstructive surgery, sarcopenia, frailty, aging skin, male hypogonadism, postmenopausal symptoms in women, atherosclerosis, hypercholesterolemia, hyperlipidemia, obesity, aplastic anemia and other hematopoietic disorders, pancreatic cancer, inflammatory arthritis and joint repair, HIV-wasting, prostate cancer, benign prostatic hyperplasia (BPH), cancer cachexia, Alzheimer's disease, muscular dystrophies, cognitive decline, sexual dysfunction, sleep apnea, depression, premature ovarian failure, and autoimmune disease. Treatment is effected by administration of a therapeutically effective amount of a compound of structural formula I to a mammal in need of such treatment. In addition, these compounds are useful as ingredients in pharmaceutical compositions alone or in combination with other active agents.

In one embodiment, the compounds of the present invention can be used to treat conditions in a male individual which are caused by androgen deficiency or which can be ameliorated by androgen replacement, including, but not limited to, osteoporosis, osteopenia, glucocorticoid-induced osteoporosis, periodontal disease, HIV-wasting, prostate cancer, cancer cachexia, obesity, arthritic conditions, anemias, such as for example, aplastic anemia, muscular dystrophies, and Alzheimer's disease, cognitive decline, sexual dysfunction, sleep apnea, depression, benign prostatic hyperplasia (BPH), and atherosclerosis, alone or in combination with other active agents. Treatment is effected by administration of a therapeutically effective amount of a compound of structural formula I to a male individual in need of such treatment.

"Arthritic condition" or "arthritic conditions" refers to a disease wherein inflammatory lesions are confined to the joints or any inflammatory conditions of the joints, most notably osteoarthritis and rheumatoid arthritis (Academic Press Dictionary of Science Technology; Academic Press; 1st edition, Jan. 15, 1992). The compounds of Formula I are also useful, alone or in combination, to treat or prevent arthritic conditions, such as Behcet's disease; bursitis and tendinitis; CPPD deposition disease; carpal tunnel syndrome; Ehlers-Danlos syndrome; fibromyalgia; gout; infectious arthritis; inflammatory bowel disease; juvenile arthritis; lupus erythematosus; lyme disease; marfan syndrome; myositis; osteoarthritis; osteogenesis imperfecta; osteonecrosis; polyarteritis; polymyalgia rheumatica; psoriatic arthritis; Raynaud's phenomenon; reflex sympathetic dystrophy syndrome; Reiter's syndrome; rheumatoid arthritis; scleroderma; and Sjogren's syndrome. An embodiment of the invention encompasses the treatment or prevention of an arthritic condition which comprises administering a therapeutically effective amount of a Compound of Formula I. A subembodiment is the treatment or prevention of osteoarthritis, which comprises administering a therapeutically effective amount of a Compound of Formula I. See: Cutolo M, Seriolo B, Villaggio B, Pizzorni C, Craviotto C, Sulli A. *Ann. N.Y. Acad. Sci.* 2002 June; 966: 131-42; Cutolo, *M. Rheum Dis Clin North Am* 2000 November; 26(4):881-95; Bijlsma J W, Van den Brink H R. Am J Reprod Immunol 1992 October-December; 28(3-4):231-4; Jansson L, Holmdahl R.; *Arthritis Rheum* 2001 September; 44(9):2168-75; and Purdie D W. Br *Med Bull* 2000; 56(3): 809-23. Also, see Merck Manual, 17th edition, pp. 449-451.

When used in combination to treat arthritic conditions, the compounds of Formula I can be used with any of the drugs disclosed herein as useful for combination therapy, or can be used with drugs known to treat or prevent arthritic conditions, such as corticosteroids, cytoxic drugs (or other disease modifying or remission inducing drugs), gold treatment, methotrexate, NSAIDs, and COX-2 inhibitors.

In another embodiment, the compounds of the present invention can be used to treat conditions in a female individual which are caused by androgen deficiency or which can be ameliorated by androgen replacement, including, but not limited to, osteoporosis, osteopenia, aging skin, glucocorticoid-induced osteoporosis, postmenopausal symptoms, periodontal disease, HIV-wasting, cancer cachexia, obesity, anemias, such as for example, aplastic anemia, muscular dystrophies, Alzheimer's disease, premature ovarian failure, cognitive decline, sexual dysfunction, depression, inflammatory arthritis and joint repair, atherosclerosis, and autoimmune disease, alone or in combination with other active agents. Treatment is effected by administration of a therapeutically effective amount of a compound of structural formula I to a female individual in need of such treatment.

The compounds of formula I are also useful in the enhancement of muscle tone in mammals, such as for example, humans. The compounds of structural formula I can also be employed as adjuncts to traditional androgen depletion therapy in the treatment of prostate cancer to restore bone, minimize bone loss, and maintain bone mineral density. In this manner, they can be employed together with traditional androgen deprivation therapy, including GnRH agonists/antagonists, such as those disclosed in P. Limonta, et al., *Exp. Opin. Invest. Drugs*, 10: 709-720 (2001); H. J. Stricker, *Urology*, 58 (Suppl. 2A): 24-27 (2001); R. P. Millar, et al., *British Medical Bulletin*, 56: 761-772 (2000); and A. V. Schally et al., *Advanced Drug Delivery Reviews*, 28: 157-169 (1997). The compounds of structural formula I can be used in combination with antiandrogens, such as flutamide, 2-hydroxyflutamide (the active metabolite of flutamide), nilutamide, and bicalutamide (Casodex™) in the treatment of prostate cancer.

Further, the compounds of the present invention can also be employed in the treatment of pancreatic cancer, either for their androgen antagonist properties or as an adjunct to an antiandrogen, such as flutamide, 2-hydroxyflutamide (the active metabolite of flutamide), nilutamide, and bicalutamide (Casodex™).

The term "treating cancer" or "treatment of cancer" refers to administration to a mammal afflicted with a cancerous condition and refers to an effect that alleviates the cancerous condition by killing the cancerous cells, but also to an effect that result in the inhibition of growth and/or metastasis of the cancer.

Compounds of structural formula I can minimize the negative effects on lipid metabolism. Therefore, considering their tissue selective androgen agonistic properties, the compounds of this invention exhibit advantages over existing approaches for hormone replacement therapy in hypogonadic (androgen deficient) male individuals.

Additionally, compounds of the present invention can increase the number of blood cells, such as red blood cells and platelets, and can be used for treatment of hematopoietic disorders, such as aplastic anemia.

In one embodiment of the invention, therapeutically effective amounts of the compound of Formula I, are administered to the mammal, to treat or improve disorders selected from enhancement of weakened muscle tone, osteoporosis, osteopenia, glucocorticoid-induced osteoporosis, periodontal disease, bone fracture, bone damage following bone reconstructive surgery, sarcopenia, frailty, aging skin, male hypogonadism, postmenopausal symptoms in women, atherosclerosis, hypercholesterolemia, hyperlipidemia, obesity, aplastic anemia and other hematopoietic disorders, pancreatic cancer, inflammatory arthritis and joint repair, HIV-wasting, prostate cancer, benign prostatic hyperplasia (BPH), cancer cachexia, Alzheimer's disease, muscular dystrophies, cognitive decline, sexual dysfunction, sleep apnea, depression, premature ovarian failure, and autoimmune disease.

In another embodiment, therapeutically effective amounts of the compound can be used to treat or improve a disorder selected from weakened muscle tone, osteoporosis, osteopenia, glucocorticoid-induced osteoporosis, periodontal disease, bone fracture, bone damage following bone reconstructive surgery, sarcopenia, Alzheimer's disease, and frailty.

In another embodiment, the compound in accordance with the invention can be used to treat or improve a disorder such as male hypogonadism, postmenopausal symptoms in women, atherosclerosis, hypercholesterolemia, hyperlipidemia, obesity, aplastic anemia and other hematopoietic disorders, pancreatic cancer, inflammatory arthritis and joint repair, HIV-wasting, prostate cancer, benign prostatic hyperplasia (BPH), cancer cachexia, muscular dystrophies, cognitive decline, sexual dysfunction, sleep apnea, depression, premature ovarian failure, and autoimmune disease.

The compounds of the present invention can be administered in their enantiomerically pure form. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

As used herein, a compound of the present invention which functions as an "agonist" of the androgen receptor can bind to the androgen receptor and initiate a physiological or a pharmacological response characteristic of that receptor. The term "tissue-selective androgen receptor modulator" refers to an androgen receptor ligand that mimics the action of a natural ligand in some tissues but not in others. A "partial agonist" is an agonist which is unable to induce maximal activation of the receptor population, regardless of the amount of compound applied. A "full agonist" induces full activation of the androgen receptor population at a given concentration. A compound of the present invention which functions as an "antagonist" of the androgen receptor can bind to the androgen receptor and block or inhibit the androgen-associated responses normally induced by a natural androgen receptor ligand.

The term "pharmaceutically acceptable salts" refers to salts prepared from pharmaceutically acceptable non-toxic bases or acids including inorganic or organic bases and inorganic or organic acids. Non-limiting representative salts derived from inorganic bases include aluminum, ammonium, calcium, copper, ferric, ferrous, lithium, magnesium, manganic salts, manganous, potassium, sodium, zinc, and the like. In one variant of the invention, the salts are chosen from the ammonium, calcium, lithium, magnesium, potassium, and sodium salts. Non-limiting examples of salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts can be prepared from pharmaceutically acceptable non-toxic acids, including inorganic and organic acids. Representative acids which can be employed include acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. In one variant, the acids are selected from citric, fumaric, hydrobromic, hydrochloric, maleic, phosphoric, sulfuric, and tartaric acids.

The preparation of the pharmaceutically acceptable salts described above and other typical pharmaceutically acceptable salts is more fully described by Berg et al., "Pharmaceutical Salts," *J. Pharm. Sci.*, 1977:66:1-19.

It would also be noted that the compounds of the present invention are potentially internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

The term "therapeutically effective amount" means the amount the compound of structural formula I that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts.

By "pharmaceutically acceptable" it is meant that the carrier, diluent or excipient must be compatible with the other ingredients of the formulation and not be deleterious to the recipient thereof.

The terms "administration of a compound" and "administering a compound" should be understood to mean providing a compound of the invention or a prodrug of a compound of the invention to the individual in need of treatment.

By the term "modulating a function mediated by the androgen receptor in a tissue selective manner" it is meant modulating a function mediated by the androgen receptor selectively (or discriminately) in anabolic (bone and/or muscular) tissue (bone and muscular) in the absence of such modulation at androgenic (reproductive) tissue, such as the prostate, testis, seminal vesicles, ovary, uterus, and other sex accessory tissues. In one embodiment, the function of the androgen receptor in anabolic tissue is activated whereas the function of the androgen receptor in androgenic tissue is blocked or suppressed. In another embodiment, the function of the androgen receptor in anabolic tissue is blocked or suppressed whereas the function of the androgen receptor in androgenic tissue is activated.

The administration of a compound of structural formula I in order to practice the present methods of therapy is carried out by administering an effective amount of the compound of structural formula I to the patient in need of such treatment or prophylaxis. The need for a prophylactic administration according to the methods of the present invention is determined via the use of well-known risk factors. The effective amount of an individual compound is determined, in the final analysis, by the physician in charge of the case, but depends on factors such as the exact disease to be treated, the severity of the disease and other diseases or conditions from which the patient suffers, the chosen route of administration, other drugs and treatments which the patient can concomitantly require, and other factors in the physician's judgment.

If formulated as a fixed dose, such combination products employ the compounds of this invention within the dosage range described below and the other pharmaceutically active agent(s) within its approved dosage range. Compounds of the instant invention can alternatively be used sequentially with known pharmaceutically acceptable agent(s) when a combination formulation is inappropriate.

Generally, the daily dosage of a compound of structural formula I can be varied over a wide range from about 0.01 to about 1000 mg per adult human per day. For example, dosages range from about 0.1 to about 200 mg/day. For oral administration, the compositions can be provided in the form of tablets containing from about 0.01 to about 1000 mg, such as for example, 0.01, 0.05, 0.1, 0.5, 1.0, 2.5, 3.0, 5.0, 6.0, 10.0, 15.0, 25.0, 50.0, 75, 100, 125, 150, 175, 180, 200, 225, and 500 milligrams of the active ingredient for the symptomatic adjustment of the dosage to the mammal to be treated.

The dose can be administered in a single daily dose or the total daily dosage can be administered in divided doses of two, three or four times daily. Furthermore, based on the properties of the individual compound selected for administration, the dose can be administered less frequently, e.g., weekly, twice weekly, monthly, etc. The unit dosage will, of course, be correspondingly larger for the less frequent administration.

When administered via intranasal routes, transdermal routes, by rectal or vaginal suppositories, or through an intravenous solution, the dosage administration will, of course, be continuous rather than intermittent throughout the dosage regimen.

Exemplifying the invention is a pharmaceutical composition comprising any of the compounds described above and a pharmaceutically acceptable carrier. Also exemplifying the invention is a pharmaceutical composition made by combining any of the compounds described above and a pharmaceutically acceptable carrier. An illustration of the invention is a process for making a pharmaceutical composition comprising combining any of the compounds described above and a pharmaceutically acceptable carrier.

Formulations of the tissue-selective androgen receptor modulator employed in the present method for medical use comprise a compound of structural formula I together with an acceptable carrier thereof and optionally other therapeutically active ingredients. The carrier must be pharmaceutically acceptable in the sense of being compatible with the other ingredients of the formulation and not being deleterious to the recipient subject of the formulation.

The present invention, therefore, further provides a pharmaceutical formulation comprising a compound of structural formula I together with a pharmaceutically acceptable carrier thereof. The formulations include those suitable for oral, rectal, intravaginal, intranasal, topical and parenteral (including subcutaneous, intramuscular and intravenous administration). In one embodiment, the formulations are those suitable for oral administration.

Suitable topical formulations of a compound of formula I include transdermal devices, aerosols, creams, solutions, ointments, gels, lotions, dusting powders, and the like. The topical pharmaceutical compositions containing the compounds of the present invention ordinarily include about 0.005% to about 5% by weight of the active compound in admixture with a pharmaceutically acceptable vehicle. Transdermal skin patches useful for administering the compounds of the present invention include those well known to those of ordinary skill in that art.

The formulations can be presented in a unit dosage form and can be prepared by any of the methods known in the art of pharmacy. All methods include the step of bringing the active compound in association with a carrier, which constitutes one or more ingredients. In general, the formulations are prepared by uniformly and intimately bringing the active compound in association with a liquid carrier, a waxy solid carrier or a finely divided solid carrier, and then, if needed, shaping the product into the desired dosage form.

Formulations of the present invention suitable for oral administration can be presented as discrete units such as capsules, cachets, tablets or lozenges, each containing a predetermined amount of the active compound; as a powder or granules; or a suspension or solution in an aqueous liquid or non-aqueous liquid, e.g., a syrup, an elixir, or an emulsion.

A tablet can be made by compression or molding, optionally with one or more accessory ingredients. Compressed tablets can be prepared by compressing in a suitable machine the active compound in a free flowing form, e.g., a powder or granules, optionally mixed with accessory ingredients, e.g., binders, lubricants, inert diluents, disintegrating agents or coloring agents. Molded tablets can be made by molding in a suitable machine a mixture of the active compound, preferably in powdered form, with a suitable carrier. Suitable binders include, without limitation, starch, gelatin, natural sugars such as glucose or beta-lactose, corn sweeteners, natural and synthetic gums such as acacia, tragacanth or sodium alginate, carboxymethyl-cellulose, polyethylene glycol, waxes and the like. Non-limiting representative lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

Oral liquid forms, such as syrups or suspensions in suitably flavored suspending or dispersing agents such as the synthetic and natural gums, for example, tragacanth, acacia, methyl cellulose and the like, can be made by adding the active compound to the solution or suspension. Additional dispersing agents which can be employed include glycerin and the like.

Formulations for vaginal or rectal administration can be presented as a suppository with a conventional carrier, i.e., a base that is nontoxic and nonirritating to mucous membranes, compatible with a compound of structural formula I, and is stable in storage and does not bind or interfere with the release of the compound of structural formula I. Suitable bases include: cocoa butter (theobroma oil), polyethylene glycols (such as carbowax and polyglycols), glycol-surfactant combinations, polyoxyl 40 stearate, polyoxyethylene sorbitan fatty acid esters (such as Tween, Myrj, and Arlacel), glycerinated gelatin, and hydrogenated vegetable oils. When glycerinated gelatin suppositories are used, a preservative such as methylparaben or propylparaben can be employed.

Topical preparations containing the active drug component can be admixed with a variety of carrier materials well known in the art, such as, e.g., alcohols, aloe vera gel, allantoin, glycerine, vitamin A and E oils, mineral oil, PPG2 myristyl propionate, and the like, to form, e.g., alcoholic solutions, topical cleansers, cleansing creams, skin gels, skin lotions, and shampoos in cream or gel formulations.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention can also be delivered by the use of monoclonal antibodies as individual carriers to which the compound molecules are coupled. The compounds of the present invention can also be coupled with soluble polymers as targetable drug carriers. Such polymers can include polyvinyl-pyrrolidone, pyran copolymer, polyhydroxypropylmethacrylamide-phenol, polyhydroxy-ethylaspartamidephenol, or polyethylene-oxide polylysine substituted with palmitoyl residues. Furthermore, the compounds of the present invention can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Formulations suitable for parenteral administration include formulations that comprise a sterile aqueous preparation of the active compound which can be isotonic with the blood of the recipient. Such formulations suitably comprise a solution or suspension of a compound that is isotonic with the blood of the recipient subject. Such formulations can contain distilled water, 5% dextrose in distilled water or saline and the active compound. Often it is useful to employ a pharmaceutically and pharmacologically acceptable acid addition salt of the active compound that has appropriate solubility for the solvents employed. Useful formulations also comprise concentrated solutions or solids comprising the active compound which on dilution with an appropriate solvent give a solution suitable for parenteral administration.

The pharmaceutical composition and method of the present invention can further comprise other therapeutically active compounds usually applied in the treatment of the above mentioned conditions, including osteoporosis, periodontal disease, bone fracture, bone damage following bone reconstructive surgery, sarcopenia, frailty, aging skin, male hypogonadism, post-menopausal symptoms in women, atherosclerosis, hypercholesterolemia, hyperlipidemia, hematopoietic disorders, such as for example, aplastic anemia, pancreatic cancer, Alzheimer's disease, inflammatory arthritis, and joint repair.

For the treatment and prevention of osteoporosis, the compounds of the present invention can be administered in combination with at least one bone-strengthening agent selected from antiresorptive agents, osteoanabolic agents, and other agents beneficial for the skeleton through mechanisms which are not precisely defined, such as calcium supplements, flavonoids, and vitamin D analogs. The conditions of periodontal disease, bone fracture, and bone damage following bone reconstructive surgery can also benefit from these combined treatments. For example, the compounds of the instant invention can be effectively administered in combination with effective amounts of other agents such as estrogens, bisphosphonates, SERMs, cathepsin K inhibitors, $\alpha v \beta 3$ integrin receptor antagonists, vacuolar ATPase inhibitors, the polypeptide osteoprotegerin, antagonists of VEGF, thiazolidinediones, calcitonin, protein kinase inhibitors, parathyroid hormone (PTH) and analogs, calcium receptor antagonists, growth hormone secretagogues, growth hormone releasing hormone, insulin-like growth factor, bone morphogenetic protein (BMP), inhibitors of BMP antagonism, prostaglandin derivatives, fibroblast growth factors, vitamin D and derivatives thereof, vitamin K and derivatives thereof, soy isoflavones, calcium salts, and fluoride salts. The conditions of periodontal disease, bone fracture, and bone damage following bone reconstructive surgery can also benefit from these combined treatments.

In one embodiment of the present invention, a compound of the instant invention can be effectively administered in combination with an effective amount of at least one bone-strengthening agent chosen from estrogen, and estrogen derivatives, alone or in combination with progestin or progestin derivatives; bisphosphonates; antiestrogens or selective estrogen receptor modulators; $\alpha v \beta 3$ integrin receptor antagonists; cathepsin K inhibitors; osteoclast vacuolar ATPase inhibitors; calcitonin; and osteoprotegerin.

In the treatment of osteoporosis, the activity of the compounds of the present invention are distinct from that of the anti-resorptive agents: estrogens, bisphosphonates, SERMs, calcitonin, cathepsin K inhibitors, vacuolar ATPase inhibitors, agents interfering with the RANK/RANKL/Osteoprotegerin pathway, p38 inhibitors or any other inhibitors of osteoclast generation or osteoclast activation. Rather than inhibiting bone resorption, the compounds of structural formula I aid in the stimulation of bone formation, acting, for example, on cortical bone, which is responsible for a significant part of bone strength. The thickening of cortical bone substantially contributes to a reduction in fracture risk, especially fractures of the hip. The combination of the tissue-SARMs of structural formula I with anti-resorptive agents such as for example estrogen or estrogen derivatives, bisphosphonates, antiestrogens, SERMs, calcitonin, $\alpha v \beta 3$ integrin receptor antagonists, HMG-CoA reductase inhibitors, vacuolar ATPase inhibitors, and cathepsin K inhibitors is particularly useful due to the complementory effect of the bone anabolic and antiresorptive actions.

Non-limiting representatives of estrogen and estrogen derivatives include steroidal compounds having estrogenic activity such as, for example, 17$\beta$-estradiol, estrone, conjugated estrogen (PREMARIN®), equine estrogen, 17$\beta$-ethynyl estradiol, and the like. The estrogen or estrogen derivative can be employed alone or in combination with a progestin or progestin derivative. Nonlimiting examples of progestin derivatives are norethindrone and medroxy-progesterone acetate.

Non-limiting examples of bisphosphonate compounds which can also be employed in combination with a compound of the present invention include:

(a) alendronate (also known as alendronic acid, 4-amino-1-hydroxybutylidene-1,1-bisphosphonic acid, alendronate sodium, alendronate monosodium trihydrate or 4-amino-1-hydroxybutylidene-1,1-bisphosphonic acid monosodium trihydrate. Alendronate is described in U.S. Pat. No. 4,922,007, to Kieczykowski et al., issued May 1, 1990; U.S. Pat. No. 5,019,651, to Kieczykowski, issued May 28, 1991; U.S. Pat. No. 5,510,517, to Dauer et al., issued Apr.

23, 1996; U.S. Pat. No. 5,648,491, to Dauer et al., issued Jul. 15, 1997, all of which are incorporated by reference herein in their entirety;

(b) [(cycloheptylamino)-methylene]-bis-phosphonate (incadronate), which is described in U.S. Pat. No. 4,970,335, to Isomura et al., issued Nov. 13, 1990, which is incorporated by reference herein in its entirety;

(c) (dichloromethylene)-bis-phosphonic acid (clodronic acid) and the disodium salt (clodronate), which are described in Belgium Patent 672,205 (1966) and *J. Org. Chem.* 32, 4111 (1967), both of which are incorporated by reference herein in their entirety;

(d) [1-hydroxy-3-(1-pyrrolidinyl)-propylidene]-bis-phosphonate (EB-1053);

(e) (1-hydroxyethylidene)-bis-phosphonate (etidronate);

(f) [1-hydroxy-3-(methylpentylamino)propylidene]-bis-phosphonate (ibandronate), which is described in U.S. Pat. No. 4,927,814, issued May 22, 1990, which is incorporated by reference herein in its entirety;

(g) (6-amino-1-hydroxyhexylidene)-bis-phosphonate (neridronate);

(h) [3-(dimethylamino)-1-hydroxypropylidene]-bis-phosphonate (olpadronate);

(i) (3-amino-1-hydroxypropylidene)-bis-phosphonate (pamidronate);

(j) [2-(2-pyridinyl)ethylidene]-bis-phosphonate (piridronate), which is described in U.S. Pat. No. 4,761,406, which is incorporated by reference in its entirety;

(k) [1-hydroxy-2-(3-pyridinyl)-ethylidene]-bis-phosphonate (risedronate);

(l) {[(4-chlorophenyl)thio]methylene}-bis-phosphonate (tiludronate), which is described in U.S. Pat. No. 4,876,248, to Breliere et al., Oct. 24, 1989, which is incorporated by reference herein in its entirety;

(m) [1-hydroxy-2-(1H-imidazol-1-yl)ethylidene]-bis-phosphonate (zoledronate); and (n) [1-hydroxy-2-imidazopyridin-(1,2-a)-3-ylethylidene]-bis-phosphonate (minodronate).

In one embodiment of the methods and compositions of the present invention, the bisphosphonate is chosen from alendronate, clodronate, etidronate, ibandronate, incadronate, minodronate, neridronate, olpadronate, pamidronate, piridronate, risedronate, tiludronate, zoledronate, pharmaceutically acceptable salts of these bisphosphonates, and mixtures thereof. In one variant, the bisphosphonate is selected from alendronate, risedronate, zoledronate, ibandronate, tiludronate, and clodronate. In a subclass of this class, the bisphosphonate is alendronate, pharmaceutically acceptable salts and hydrates thereof, and mixtures thereof. A particular pharmaceutically acceptable salt of alendronate is alendronate monosodium. Pharmaceutically acceptable hydrates of alendronate monosodium include the monohydrate and the trihydrate. A particular pharmaceutically acceptable salt of risedronate is risedronate monosodium. Pharmaceutically acceptable hydrates of risedronate monosodium include the hemi-pentahydrate.

Still further, antiestrogenic compounds such as raloxifene (see, e.g., U.S. Pat. No. 5,393,763), clomiphene, zuclomiphene, enclomiphene, nafoxidene, CI-680, CI-628, CN-55, 945-27, Mer-25, U-11,555A, U-100A, and salts thereof, and the like (see, e.g., U.S. Pat. Nos. 4,729,999 and 4,894,373) can be employed in combination with a compound of structural formula I in the methods and compositions of the present invention. These agents are also known as SERMs, or selective estrogen receptor modulators, agents known in the art to prevent bone loss by inhibiting bone resorption via pathways believed to be similar to those of estrogens.

Non-limiting representatives of SERMs include, for example, tamoxifen, raloxifene, lasofoxifene, toremifene, azorxifene, EM-800, EM-652, TSE 424, clomiphene, droloxifene, idoxifene, and levormeloxifene [Goldstein, et al., "A pharmacological review of selective estrogen receptor modulators," *Human Reproduction Update*, 6: 212-224 (2000); Lufkin, et al., *Rheumatic Disease Clinics of North America* 27: 163-185 (2001), and "Targeting the Estrogen Receptor with SERMs," *Ann. Rep. Med. Chem.* 36: 149-158 (2001)].

αvβ3 Integrin receptor antagonists suppress bone resorption and can be employed in combination with the SARMs of structural formula I for the treatment of bone disorders including osteoporosis. Peptidyl as well as peptidomimetic antagonists of the αvβ3 integrin receptor have been described both in the scientific and patent literature. For example, reference is made to W. J. Hoekstra and B. L. Poulter, *Curr. Med. Chem.* 5: 195-204 (1998) and references cited therein; WO 95/32710; WO 95/37655; WO 97/01540; WO 97/37655; WO 98/08840; WO 98/18460; WO 98/18461; WO 98/25892; WO 98/31359; WO 98/30542; WO 99/15506; WO 99/15507; WO 00/03973; EP 853084; EP 854140; EP 854145; U.S. Pat. Nos. 5,204,350; 5,217,994; 5,639,754; 5,741,796; 5,780,426; 5,929,120; 5,952,341; 6,017,925; and 6,048,861.

Other αvβ3 antagonists are described in R. M. Keenan et al., *J. Med. Chem.* 40: 2289-2292 (1997); R. M. Keenan et al., *Bioorg. Med. Chem. Lett.* 8: 3165-3170 (1998); and R. M. Keenan et al., *Bioorg. Med. Chem. Lett.* 8: 3171-3176 (1998).

Other non-limiting representative examples of published patent and patent applications that describe various αvβ3 integrin receptor antagonists include: those comprising benzazepine, benzodiazepine and benzocycloheptene—PCT Patent Application Nos. WO 96/00574, WO 96/00730, WO 96/06087, WO 96/26190, WO 97/24119, WO 97/24122, WO 97/24124, WO 98/14192, WO 98/15278, WO 99/05107, WO 99/06049, WO 99/15170, WO 99/15178, WO 97/34865, WO 99/15506, and U.S. Pat. No. 6,159,964; those comprising dibenzpcyclopheptene, and dibenzoxapine—PCT Patent Application Nos. WO 97/01540, WO 98/30542, WO 99/11626, WO 99/15508, and U.S. Pat. Nos. 6,008,213 and 6,069,158; those having a phenol constraint—PCT Patent Application Nos. WO 98/00395, WO 99/32457, WO 99/37621, WO 99/44994, WO 99/45927, WO 99/52872, WO 99/52879, WO 99/52896, WO 00/06169, European Patent Nos. EP 0 820,988, EP 0 820,991, and U.S. Pat. Nos. 5,741,796, 5,773,644, 5,773,646, 5,843,906, 5,852,210, 5,929,120, 5,952,281, 6,028,223 and 6,040,311; those having a monocyclic ring constraint—PCT Patent Application Nos. WO 99/26945, WO 99/30709, WO 99/30713, WO 99/31099, WO 99/59992, WO 00/00486, WO 00/09503, European Patent Nos. EP 0 796,855, EP 0 928,790, EP 0 928,793, and U.S. Pat. Nos. 5,710,159, 5,723,480, 5,981,546, 6,017,926, and 6,066,648; and those having a bicyclic ring constraint—PCT Patent Application Nos. WO 98/23608, WO 98/35949, and WO 99/33798, European Patent No. EP 0 853,084, and U.S. Pat. Nos. 5,760,028, 5,919,792, and 5,925,655.

Cathepsin K, formerly known as cathepsin O2, is a cysteine protease and is described in PCT International Application Publication No. WO 96/13523; U.S. Pat. Nos. 5,501,969 and 5,736,357; all of which are incorporated by reference herein in their entirety. Cysteine proteases, specifically cathepsins, are linked to a number of disease conditions, such as tumor metastasis, inflammation, arthritis, and bone remodeling. At acidic pH's, cathepsins can degrade type-I collagen. Cathepsin protease inhibitors can inhibit osteoclastic bone resorption by inhibiting the degradation of collagen fibers and are thus useful in the treatment of bone resorption diseases, such as osteoporosis. Non-limiting examples of cathespin K inhibitors can be found in PCT International Publications WO 01/49288 and WO 01/77073.

Members of the class of HMG-CoA reductase inhibitors, known as the "statins," have been found to trigger the growth of new bone, replacing bone mass lost as a result of osteoporosis (see *The Wall Street Journal*, Friday, Dec. 3, 1999, page B1). Therefore, the statins hold promise for the treatment of bone resorption. Examples of HMG-CoA reductase inhibitors include statins in their lactonized or dihydroxy open acid forms and pharmaceutically acceptable salts and esters thereof, including but not limited to lovastatin (see U.S. Pat. No. 4,342,767); simvastatin (see U.S. Pat. No. 4,444, 784); dihydroxy open-acid simvastatin, particularly the ammonium or calcium salts thereof; pravastatin, particularly the sodium salt thereof (see U.S. Pat. No. 4,346,227); fluvastatin, particularly the sodium salt thereof (see U.S. Pat. No. 5,354,772); atorvastatin, particularly the calcium salt thereof (see U.S. Pat. No. 5,273,995); cerivastatin, particularly the sodium salt thereof (see U.S. Pat. No. 5,177,080), rosuvastatin, also known as ZD-4522 (see U.S. Pat. No. 5,260,440) and pitavastatin, also referred to as NK-104, itavastatin, or nisvastatin (see PCT international application publication number WO 97/23200).

Osteoclast vacuolar ATPase inhibitors, also called proton pump inhibitors, can be employed together with the SARMs of structural formula I. The proton ATPase which is found on the apical membrane of the osteoclast has been reported to play a significant role in the bone resorption process. Therefore, this proton pump represents an attractive target for the design of inhibitors of bone resorption which are potentially useful for the treatment and prevention of osteoporosis and related metabolic diseases [see C. Farina et al., *DDT*, 4: 163-172 (1999)].

The angiogenic factor VEGF has been shown to stimulate the bone-resorbing activity of isolated mature rabbit osteoclasts via binding to its receptors on osteoclasts [see M. Nakagawa et al., *FEBS Letters*, 473: 161-164 (2000)]. Therefore, the development of antagonists of VEGF binding to osteoclast receptors, such as KDR/Flk-1 and Flt-1, can provide yet a further approach to the treatment or prevention of bone resorption.

Activators of the peroxisome proliferator-activated receptor-γ (PPARγ), such as the thiazolidinediones (TZD's), inhibit osteoclast-like cell formation and bone resorption in vitro. Results reported by R. Okazaki et al. in *Endocrinology*, 140: 5060-5065 (1999) point to a local mechanism on bone marrow cells as well as a systemic one on glucose metabolism. Nonlimiting examples of PPARγ, activators include the glitazones, such as troglitazone, pioglitazone, rosiglitazone, and BRL 49653.

Calcitonin can also be employed together with the SARMs of structural formula I. Calcitonin is preferentially employed as salmon nasal spray (Azra et al., Calcitonin. 1996. In: J. P. Bilezikian, et al., Ed., *Principles of Bone Biology*, San Diego: Academic Press; and Silverman, "Calcitonin," *Rheumatic Disease Clinics of North America* 27: 187-196, 2001)

Protein kinase inhibitors can also be employed together with the SARMs of structural formula I. Kinase inhibitors include those disclosed in WO 01/17562 and are in one embodiment selected from inhibitors of p38. Non-limiting examples of p38 inhibitors useful in the present invention include SB 203580 [Badger et al., *J. Pharmacol. Exp. Ther.*, 279: 1453-1461 (1996)].

Osteoanabolic agents are those agents that are known to build bone by increasing the production of the bone protein matrix. Such osteoanabolic agents include, for example, parathyroid hormone (PTH) and fragments thereof, such as naturally occurring PTH (1-84), PTH (1-34), analogs thereof, native or with substitutions and particularly parathyroid hormone subcutaneous injection. PTH has been found to increase the activity of osteoblasts, the cells that form bone, thereby promoting the synthesis of new bone (*Modern Drug Discovery*, Vol. 3, No. 8, 2000). An injectable recombinant form of human PTH, Forteo (teriparatide), has received regulatory approval in the U.S. for the treatment of osteoporosis.

Also useful in combination with the SARMs of the present invention are calcium receptor antagonists which induce the secretion of PTH as described by Gowen et al., *J. Clin. Invest*. 105: 1595-604 (2000).

Additional osteoanabolic agents include growth hormone secretagogues, growth hormone, growth hormone releasing hormone and the like can be employed with the compounds according to structural formula I for the treatment of osteoporosis. Representative growth hormone secretagogues are disclosed in U.S. Pat. Nos. 3,239,345, 4,036,979, 4,411, 890, 5,206,235, 5,283,241, 5,284,841, 5,310,737, 5,317,017, 5,374,721, 5,430,144, 5,434,261, 5,438,136, 5,494,919, 5,494,920, 5,492,916 and 5,536,716; European Patent Pub. Nos. 0,144,230 and 0,513,974; PCT Patent Pub. Nos. WO 94/07486, WO 94/08583, WO 94/11012; WO 94/13696, WO 94/19367, WO 95/03289, WO 95/03290, WO 95/09633, WO 95/11029, WO 95/12598, WO 95/13069, WO 95/14666, WO 95/16675, WO 95/16692, WO 95/17422, WO 95/17423, WO 95/34311, and WO 96/02530; articles, *Science*, 260, 1640-1643 (Jun. 11, 1993); *Ann. Rep. Med. Chem.*, 28: 177-186 (1993); *Bioorg. Med. Chem. Lett.*, 4: 2709-2714 (1994); and *Proc. Natl. Acad. Sci. USA*, 92: 7001-7005 (1995).

Insulin-like growth factor (IGF) can also be employed together with the SARMs of structural formula I. Insulin-like growth factors can be selected from Insulin-like Growth Factor I, alone or in combination with IGF binding protein 3 and IGF II [See Johannson and Rosen, "The IGFs as potential therapy for metabolic bone diseases," 1996, In: Bilezikian, et al., Ed., *Principles of Bone Biology*, San Diego: Academic Press; and Ghiron et al., *J. Bone Miner. Res*. 10: 1844-1852 (1995)].

Bone morphogenetic protein (BMP) can also be employed together with the SARMs of structural formula I. Bone morphogenetic protein includes BMP 2, 3, 5, 6, 7, as well as related molecules TGF beta and GDF 5 [Rosen et al., "Bone morphogenetic proteins," 1996. In: J. P. Bilezikian, et al., Ed., *Principles of Bone Biology*, San Diego: Academic Press; and Wang E A, *Trends Biotechnol.*, 11: 379-383 (1993)].

Inhibitors of BMP antagonism can also be employed together with the SARMs of structural formula I. In one embodiment, BMP antagonist inhibitors are chosen from inhibitors of the BMP antagonists SOST, noggin, chordin, gremlin, and dan [see Massague and Chen, "Controlling TGF-beta signaling," *Genes Dev.*, 14: 627-644, 2000; Aspenberg et al., *J. Bone Miner. Res*. 16: 497-500, 2001; and Brunkow et al., *Am. J. Hum. Genet*. 68: 577-89 (2001)].

The tissue-selective androgen receptor modulators of the present invention can also be combined with the polypeptide osteoprotegerin for the treatment of conditions associated with bone loss, such as osteoporosis. The osteoprotegerin can be selected from mammalian osteoprotegerin and human osteoprotegerin. The polypeptide osteoprotegerin, a member of the tumor necrosis factor receptor super-family, is useful to treat bone diseases characterized by increased bone loss, such as osteoporosis. Reference is made to U.S. Pat. No. 6,288, 032, which is incorporated by reference herein in its entirety.

Prostaglandin derivatives can also be employed together with the SARMs of structural formula I. Non-limiting representatives of prostaglandin derivatives are selected from agonists of prostaglandin receptors EP1, EP2, EP4, FP, IP and derivatives thereof [Pilbeam et al., "Prostaglandins and bone metabolism," 1996. In: Bilezikian, et al. Ed. Principles of Bone Biology, San Diego: Academic Press; Weinreb et al., *Bone*, 28: 275-281 (2001)].

Fibroblast growth factors can also be employed together with the SARMs of structural formula I. Fibroblast growth factors include aFGF, bFGF and related peptides with FGF activity [Hurley Florkiewicz, "Fibroblast growth factor and vascular endothelial growth factor families," 1996. In: J. P. Bilezikian, et al., Ed. Principles of Bone Biology, San Diego: Academic Press].

In addition to bone resorption inhibitors and osteoanabolic agents, there are also other agents known to be beneficial for the skeleton through mechanisms which are not precisely defined. These agents can also be favorably combined with the SARMs of structural formula I.

Vitamin D and vitamin D derivatives can also be employed together with the SARMs of structural formula I. Vitamin D and vitamin D derivatives include, for example, natural vitamin D, 25-OH-vitamin D3, 1α,25(OH)$_2$ vitamin D3, 1α-OH-vitamin D3, 1α-OH-vitamin D2, dihydrotachysterol, 26,27-F6-1α,25(OH)$_2$ vitamin D3, 19-nor-1α,25(OH)$_2$ vitamin D3, 22-oxacalcitriol, calcipotriol, 1α,25(OH)$_2$-16-ene-23-yne-vitamin D3 (Ro 23-7553), EB1089,20-epi-1α,25(OH)$_2$ KH1060, ED71, 1α,24(S)—(OH)$_2$ vitamin D3, 1α,24(R)—(OH)$_2$ vitamin D3 [See, Jones G., "Pharmacological mechanisms of therapeutics: vitamin D and analogs," 1996. In: J. P. Bilezikian, et al. Ed. Principles of Bone Biology, San Diego: Academic Press].

Vitamin K and Vitamin K derivatives can also be employed together with the SARMs of structural formula I. Vitamin K and vitamin K derivatives include menatetrenone (vitamin K2) [see Shiraki et al., *J. Bone Miner. Res.*, 15: 515-521 (2000)].

Soy isoflavones, including ipriflavone, can be employed together with the SARMs of structural formula I.

Fluoride salts, including sodium fluoride (NaF) and monosodium fluorophosphate (MFP), can also be employed together with the SARMs of structural formula I. Dietary calcium supplements can also be employed together with the SARMs of structural formula I. Dietary calcium supplements include calcium carbonate, calcium citrate, and natural calcium salts (Heaney. Calcium. 1996. In: J. P. Bilezikian, et al., Ed., Principles of Bone Biology, San Diego: Academic Press).

Daily dosage ranges for bone resorption inhibitors, osteoanabolic agents and other agents which can be used to benefit the skeleton when used in combination with a compound of structural formula I are those which are known in the art. In such combinations, generally the daily dosage range for the SARMs of structural formula I ranges from about 0.01 to about 1000 mg per adult human per day, such as for example, from about 0.1 to about 200 mg/day. However, adjustments to decrease the dose of each agent can be made due to the increased efficacy of the combined agent.

In particular, when a bisphosphonate is employed, dosages from about 2.5 to about 100 mg/day (measured as the free bisphosphonic acid) are appropriate for treatment, such as for example ranging from 5 to 20 mg/day, or about 10 mg/day. Prophylactically, doses of about 2.5 to about 10 mg/day and especially about 5 mg/day should be employed. For reduction in side-effects, it can be desirable to administer the combination of a compound of structural formula I and the bisphosphonate once a week. For once weekly administration, doses ranging from about 15 mg to about 700 mg per week of bisphosphonate and from about 0.07 to about 7000 mg of a compound of structural formula I can be employed, either separately, or in a combined dosage form. A compound of structural formula I can be favorably administered in a controlled-release delivery device, particularly for once weekly administration.

For the treatment of atherosclerosis, hypercholesterolemia, and hyperlipidemia, the compounds of structural formula I can be effectively administered in combination with one or more additional active agents. The additional active agent or agents can be chosen from lipid-altering compounds such as HMG-CoA reductase inhibitors, agents having other pharmaceutical activities, and agents that have both lipid-altering effects and other pharmaceutical activities. Non-limiting examples of HMG-CoA reductase inhibitors include statins in their lactonized or dihydroxy open acid forms and pharmaceutically acceptable salts and esters thereof, including but not limited to lovastatin (see U.S. Pat. No. 4,342,767); simvastatin (see U.S. Pat. No. 4,444,784); dihydroxy open-acid simvastatin, particularly the ammonium or calcium salts thereof; pravastatin, particularly the sodium salt thereof (see U.S. Pat. No. 4,346,227); fluvastatin, particularly the sodium salt thereof (see U.S. Pat. No. 5,354,772); atorvastatin, particularly the calcium salt thereof (see U.S. Pat. No. 5,273,995); cerivastatin, particularly the sodium salt thereof (see U.S. Pat. No. 5,177,080), and nisvastatin, also referred to as NK-104 (see PCT international application publication number WO 97/23200).

Additional active agents which can be employed in combination with a compound of structural formula I include, but are not limited to, HMG-CoA synthase inhibitors; squalene epoxidase inhibitors; squalene synthetase inhibitors (also known as squalene synthase inhibitors), acyl-coenzyme A: cholesterol acyltransferase (ACAT) inhibitors including selective inhibitors of ACAT-1 or ACAT-2 as well as dual inhibitors of ACAT-1 and -2; microsomal triglyceride transfer protein (MTP) inhibitors; probucol; niacin; cholesterol absorption inhibitors, such as SCH-58235, also known as ezetimibe and 1-(4-fluorophenyl)-3(R)-[3(S)-(4-fluorophenyl)-3-hydroxypropyl)]-4(S)-(4-hydroxyphenyl)-2-azetidinone, which is described in U.S. Pat. Nos. 5,767,115 and 5,846,966; bile acid sequestrants; LDL (low density lipoprotein) receptor inducers; platelet aggregation inhibitors, for example glycoprotein IIb/IIIa fibrinogen receptor antagonists and aspirin; human peroxisome proliferator activated receptor gamma (PPARγ), agonists, including the compounds commonly referred to as glitazones, for example troglitazone, pioglitazone and rosiglitazone and, including those compounds included within the structural class known as thiazolidinediones as well as those PPARγ, agonists outside the thiazolidinedione structural class; PPARα agonists, such as clofibrate, fenofibrate including micronized fenofibrate, and gemfibrozil; PPAR dual α/γ agonists; vitamin B$_6$ (also known as pyridoxine) and the pharmaceutically acceptable salts thereof such as the HCl salt; vitamin B$_{12}$ (also known as cyanocobalamin); folic acid or a pharmaceutically acceptable salt or ester thereof such as the sodium salt and the methylglucamine salt; anti-oxidant vitamins such as vitamin C and E and beta carotene; beta-blockers; angiotensin II antagonists such as losartan; angiotensin converting enzyme inhibitors, such as enalapril and captopril; calcium channel blockers, such as nifedipine and diltiazem; endothelin antagonists; agents such as LXR ligands that enhance ABC1 gene expression; bisphosphonate compounds, such as alendronate sodium; and cyclooxygenase-2 inhibitors, such as rofecoxib and celecoxib, as well as other agents known to be useful in the treatment of these conditions.

Daily dosage ranges for HMG-CoA reductase inhibitors when used in combination with the compounds of structural formula I correspond to those which are known in the art. Similarly, daily dosage ranges for the HMG-CoA synthase inhibitors; squalene epoxidase inhibitors; squalene synthetase inhibitors (also known as squalene synthase inhibitors), acyl-coenzyme A: cholesterol acyltransferase (ACAT) inhibitors including selective inhibitors of ACAT-1 or ACAT-2 as well as dual inhibitors of ACAT-1 and -2; microsomal triglyceride transfer protein (MTP) inhibitors; probucol; niacin; cholesterol absorption inhibitors including ezetimibe; bile acid sequestrants; LDL (low density lipoprotein) receptor inducers; platelet aggregation inhibitors, including glycoprotein IIb/IIIa fibrinogen receptor antagonists and aspirin; human peroxisome proliferator activated receptor gamma (PPARγ) agonists; PPARα agonists; PPAR dual α/γ agonists; vitamin B$_6$; vitamin B$_{12}$; folic acid; anti-oxidant vitamins; beta-blockers; angiotensin II antagonists; angiotensin converting enzyme inhibitors; calcium channel blockers; endothelin antagonists; agents such as LXR ligands that enhance ABC1 gene expression; bisphosphonate compounds; and cyclooxygenase-2 inhibitors also correspond to those which are known in the art, although due to the combined action with the compounds of structural formula I, the dosage can be somewhat lower when administered in combination.

One embodiment of the invention is a method for affecting a bone turnover marker in a mammal comprising administering a therapeutically effective amount of a compound according to formula I. Non-limiting examples of bone turnover markers can be selected from urinary C-telopeptide degradation products of type I collagen (CTX), urinary N-telopeptide cross-links of type I collagen (NTX), osteocalcin (bone G1a protein), dual energy x-ray absorptionmetry (DXA), bone specific alkaline phosphatase (BSAP), quantitative ultrasound (QUS), and deoxypyridinoline (DPD) crosslinks.

In accordance with the method of the present invention, the individual components of the combination can be administered separately at different times during the course of therapy or concurrently in divided or single combination forms. The instant invention is therefore to be understood as embracing all such regimes of simultaneous or alternating treatment and the term "administering" is to be interpreted accordingly. It will be understood that the scope of combinations of the compounds of this invention with other agents useful for treating diseases caused by androgen deficiency or that can be ameliorated by addition of androgen.

Abbreviations Used in the Description of the Preparation of the Compounds of the Present Invention:
DEA N,N-diethylamine
DHT Dihydrotestosterone
DMEM Dulbecceo modified eagle media
DMSO Dimethyl sulfoxide
DMF N,N-Dimethylformamide
EDC 1-(3-Dimethylaminopropyl)-3-ethylcarbodiimide HCl
EDTA Ethylenediaminetetraacetic acid
EtOAc Ethyl acetate
EtOH Ethanol
FCS Fetal calf serum
FN(SO$_2$Ph)$_2$ N-Fluorobenzenesulfonimide
HEPES (2-Hydroxyethyl)-1-piperazineethanesulfonic acid
HOAt 1-hydroxy-7-azabenzotriazole
HOBt N-hydroxybenzotriazole
HPLC High-performance liquid chromatography
IPA Isopropyl alcohol
LCMS Liquid chromotography/mass spectroscopy
LDA Lithium diisopropylamide
LG Leaving group
MeOH Methanol
MgSO$_4$ Magnesium sulfate
NBS N-bromosuccinimide
NMM N-methylmorpholine
N-CBz-analine N-Carbobenzyloxyglycine
n-Bu4NI Tetra-n-butylammonium iodide
Rt or rt Room temperature
THF Tetrahydrofuran
TLC Thin-layer chromatography The compounds of this invention may be prepared by employing reactions as shown in the following schemes, in addition to other standard manipulations that are known in the literature or exemplified in the experimental procedures. The illustrative schemes below, therefore, are not limited by the compounds listed or by any particular substituents employed for illustrative purposes. Substituent numbering as shown in the schemes does not necessarily correlate to that used in the claims and often, for clarity, a single substituent is shown attached to the compound in place of multiple substituents which are allowed under the definitions of Formula I defined previously.

Schemes A-C provide general guidelines for making compounds of Formula I. Scheme A illustrates a process for synthesizing the platform, 2-Fluoro-4-methyl-3-oxo-4-aza-5α-androst-1-ene-17β-carboxylic acid methyl ester. Scheme B illustrates the synthesis of the various 3H-imidazo[4,5-b]pyridin-2-yl)]amines. Scheme C illustrates the coupling of the fluorinated 4-azasteroid derivative with the amine to form the compounds described in Formula I.

It should be noted that in Scheme A, the selection of the particular leaving group, LG, will of course depend upon the particular substituent class that is incorporated onto the core structure. Selection and application of leaving groups is a common practice in the synthetic organic chemical art and this information is readily known and accessible to one skilled in the art. See for example, *Organic Synthesis*, Smith, M, McGraw-Hill INC, 1994, New York. ISBN 0-07-048716-2.

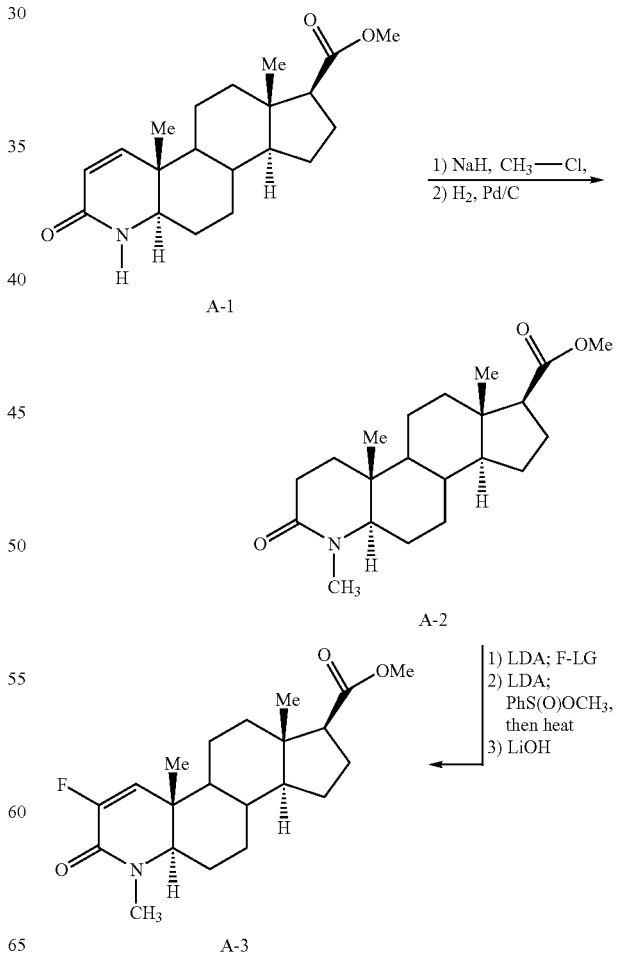

SCHEME A

SCHEME B
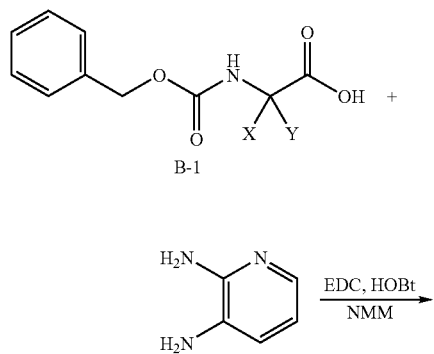
SCHEME C
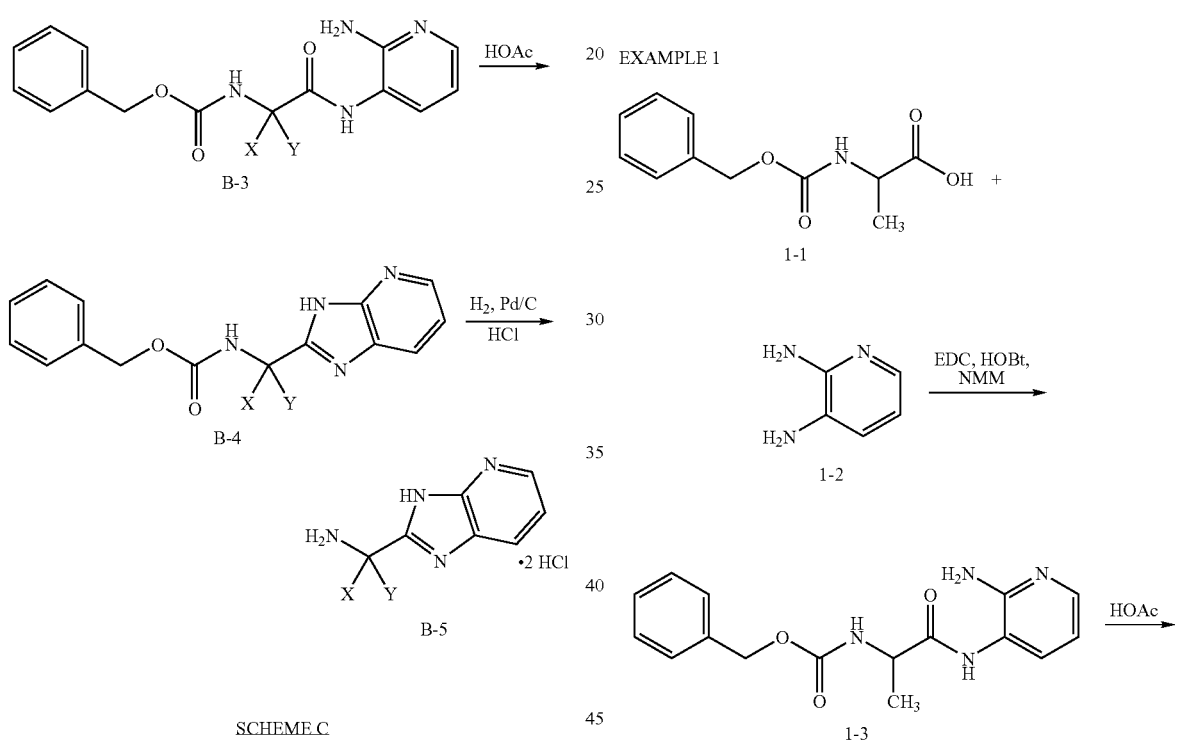
EXAMPLE 1
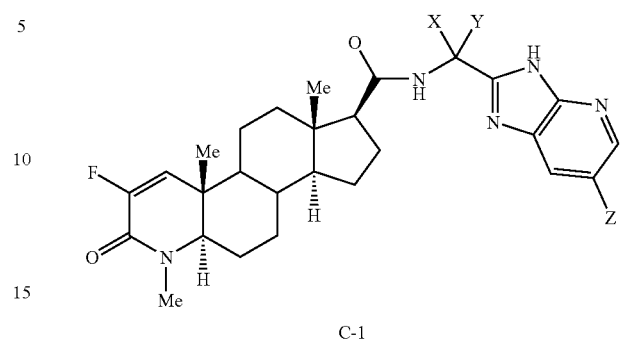
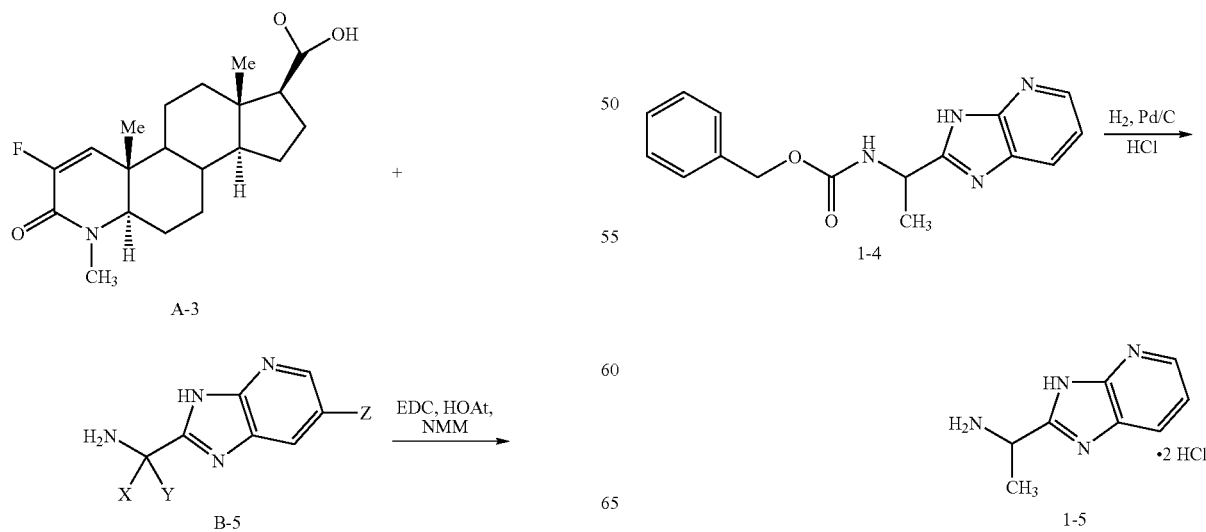

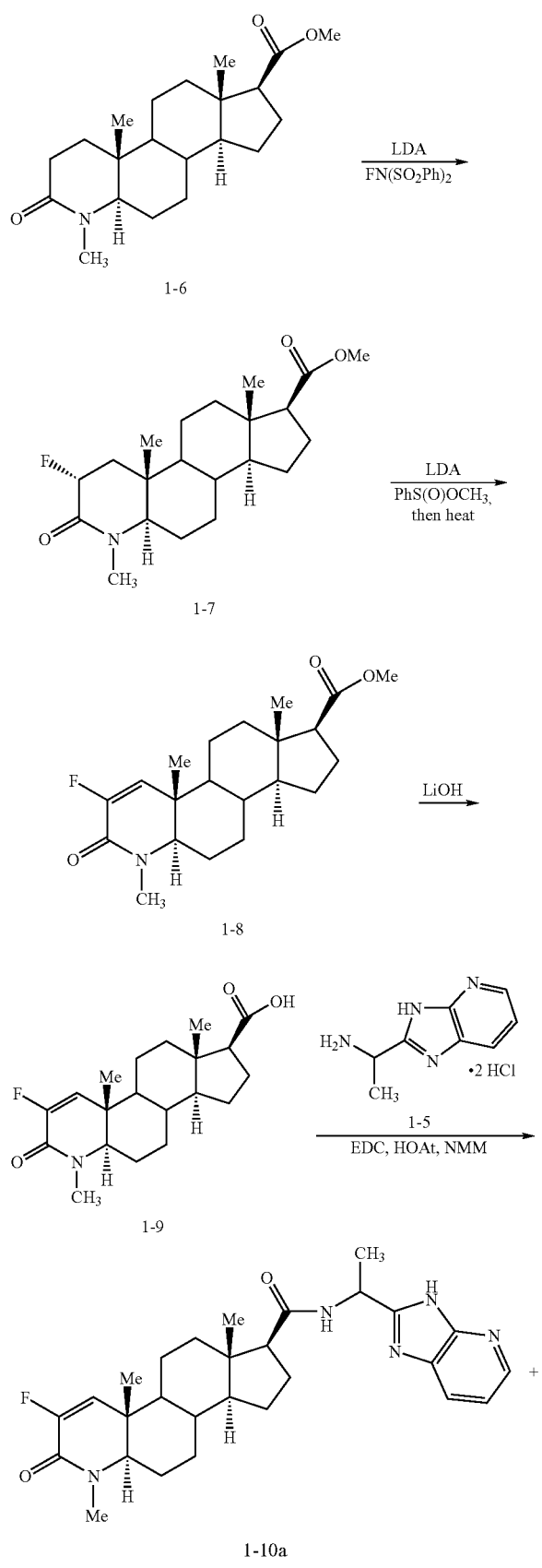
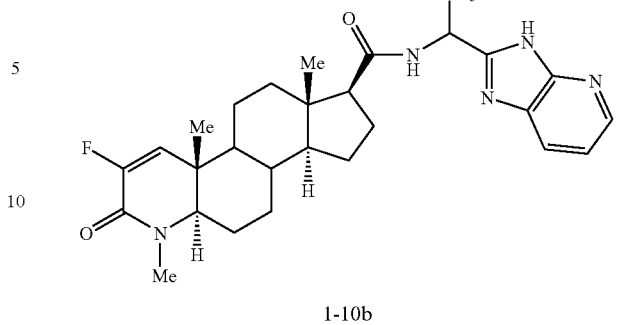

Step A: N¹-(3-aminopyridin-2-yl)-N²-(carboxylbenzoyl)alaninamide (1-3)

N-CBz-alanine (1-1, 87.7 g, 392 mmol), 2,3-diaminopyridine (1-2, 47.16 g, 432 mmol), EDC (90.4 g, 471 mmol), NMM (79.5 g, 785 mmol) and HOBt (63.7 g, 471 mmol) were mixed in acetonitrile (600 mL) and stirred for 18 hours. The solvent was then removed on a rotary evaporator, and the thick oily residue diluted with 1.5 L water containing 50 grams solid potassium carbonate and 100 g sodium chloride. Extracted with 3×600 mL EtOAc. Combined organics washed with water, brine, dried over MgSO4. Evaporation of the solvent gave a dark brown oil. The residue was reduced from a mixture of 1,4-dioxane and toluene to remove any NMM to produce 1-3 (112 g, 91%) as a brown oil. MS calculated M+H, 315.4, found 315.4.

Step B: Benzyl[1-(3H-imidazo[4,5-b]pyridin-2-yl)ethyl]carbamate (1-4)

Amide 1-3 (112 g, 356 mmol) was dissolved in glacial acetic acid (750 mL) and heated at reflux for 15 hours. The solvent was then removed on a rotary evaporator. The thick oily residue was reduced from a solution in 1,4-dioxane. The resulting brown oil solidified upon standing to produce 1-4 (110 g, 104%) as a brown solid. MS calculated M+H, 297.3, found 297.3.

Step C: [1-(3H-imidazo[4,5-b]pyridin-2-yl)ethyl]amine dihydrochloride (1-5)

A mixture of 1-4 (100 g, 318 mmol), acetic acid (500 mL), ethanol (500 mL) and 10% palladium on carbon (20 grams) was stirred under a balloon of hydrogen for 48 hours. The mixture was filtered through a pad of celite, and the solvents removed on a rotary evaporator. The resulting thick oily residue was reduced from a solution in 1,4-dioxane, then resuspended in dioxane and 4HCl in dioxane (200 mL) was added. After stirring for 2 hours, the resulting suspension was filtered and solid collected and dried under vacuum to provide 1-5 (70 g, 94%) as a light brown solid.

MS calculated M+H, 163.3, found 163.3.

Step D: 2α-Fluoro-4-methyl-3-oxo-4-aza-5α-androstane-17β-carboxylic acid methyl ester (1-7)

To a solution of 1-6 (7.5 g, 21.6 mmol) in THF (100 mL) at −78° C. was added a solution of 1.5 M LDA in THF (17.3 mL, 25.9 mmol) dropwise over 20 min and then stirred 1 h. A solution of FN(SO₂Ph)₂ (10.2 g, 32.4 mmol) in THF (40 mL) was then added over 20 min. After 30 min, the cooling bath was removed and the reaction was stirred for 14 h. Et₂O was added, and the mixture washed with water, saturated aqueous sodium hydrogencarbonate, brine, dried (MgSO₄) and then concentrated. Chromatography on silica gel (hexanes to EtOAc as eluent) gave 1-7 (4.2 g) as a colorless solid.

MS calculated M+H: 366, found 366.1.

Step E: 2-Fluoro-4-methyl-3-oxo-4-aza-5α-androst-1-ene-17β-carboxylic acid methyl ester (1-8)

To a solution of 1-7 (30 g, 82.1 mmol) in THF (400 mL) at −78° C. was added a solution of 1.5 M LDA in THF (71.1 mL, 107 mmol) dropwise over 30 min and then stirred 1 h. Methyl benzenesulfinate (19.23 g, 123 mmol) was then added over 15 min. After 30 min, the cooling bath was removed and the reaction was stirred for 1 h. Et₂O was added, and the mixture washed with water, saturated aqueous sodium hydrogencarbonate, brine, dried (MgSO₄) and then concentrated. The residue was dissolved in toluene (200 mL) and heated at reflux for 2 h. Solvent evaporation and chromatography of the residue on silica gel (hexanes to 50% EtOAc/hexanes as eluent) gave 1-8 (20.4 g) as a pale yellow solid. MS calculated M+H, 364.1, found 364.1.

Step F: 2-Fluoro-4-methyl-3-oxo-4-aza-5α-androst-1-ene-17β-carboxylic acid (1-9)

To a solution of 1-8 (2.4 g, 6.6 mmol) in 1,4-dioxane (50 mL) was added a solution of lithium hydroxide (0.41 g, 9.9 mmol) in water (20 mL), and the mixture heated at 100° C. for 3 h. After cooling, the mixture was diluted with ethyl acetate and then washed with 1N HCl, brine, dried (MgSO₄) and then concentrated to give 1-9 (2.2 g) as a pale yellow solid. MS calculated M+H: 350, found 350.

Step G: N-[1-(3H-imidazo[4,5-b]pyridin-2-yl)ethyl]-2-fluoro-4-methyl-3-oxo-4-aza-5α-androst-1-en-17β-carboxamide (1-10a and 1-10b)

A mixture of 1-9 (0.5 g, 1.43 mmol), EDC (0.329 g, 1.717 mmol), HOAt (0.234 g, 1.717 mmol), NMM (0.629 mL, 5.723 mmol) and 1-5 (0.34 g, 1.431 mmol) in DMF (5 mL) was stirred at ambient temperature for 14 hours. The mixture was diluted with water, filtered, and the solids washed with water and then dried under vacuum. Chromatography on 5×10 cm CHIRACEL AD column, eluting with 70:30 IPA/ 0.1% DEA in hexanes, 100 ml/min, gave first 1-10a (retention time 21 minutes, 0.15 g, 21%) as a white solid and then 1-10b (retention time 28 minutes, 0.23 g, 31.9%) as a white solid. The stereochemical configuration of the carbon atom adjacent to the imidazole ring in compound 1-10a was determined to be (R) by x-ray analysis as described in Example 4.

1-10a: ¹H NMR (500 MHz, CDCl₃) 8.38 (m, 1H), 8.03 (m, 1H), 7.26 (m, 1H, J=12 Hz), 5.44 (t, 1H, J=7 Hz), 3.41 (dd, 1H, J=4 Hz, 13 Hz), 2.98 (s, 3H), 2.21 (m, 2H), 1.98 (m, 2H), 1.86 (m, 1H), 1.76 (d, 3H, J=7 Hz), 1.59-1.75 (m, 5H), 1.28-1.44 (m, 4H), 1.10 (m, 2H), 0.98 (s, 3H), 0.74 (s, 3H). MS calculated M+H, 494.2926 found 494.2909.

1-10b ¹H NMR (500 MHz, CDCl₃) 8.39 (m, 1H), 8.04 (m, 1H), 7.26 (m, 1H, J=12 Hz), 5.42 (m, 1H), 3.39 (m, 1H), 2.97 (s, 3H), 2.23 (m, 2H), 1.97 (m, 1H), 1.86 (m, 2H), 1.76 (d, 3H, J=7 Hz), 1.71 (m, 2H), 1.55 (m, 2H), 1.25-1.4 (m, 4H), 0.99-1.14 (m, 3H), 0.92 (s, 3H), 0.62 (s, 3H). MS calculated M+H, 494.2926 found 494.2921.

Examples 2-4 in Table 1 were prepared in a similar manner as compound 1-10, but using the appropriate amine to generate the final desired product.

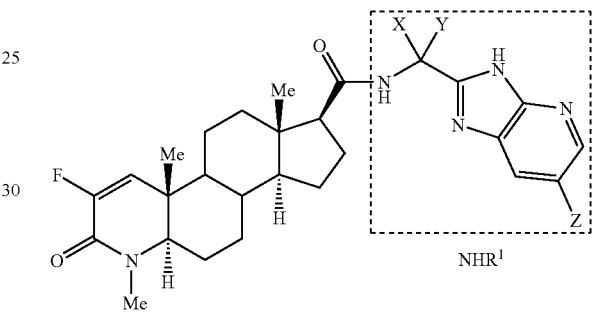

TABLE 1

| Ex. | NHR¹ | Name | Mass spectrum Measured [M + H] |
|---|---|---|---|
| 1 | (1-10a) | N-[1(R)-(3H-imidazo[4,5-b]pyridin-2-yl)ethyl]-2-fluoro-4-methyl-3-oxo-4-aza-5α-androst-1-en-17β-carboxamide | 494.2909 |
| 2 | (1-10b) | N-[1(S)-(3H-imidazo[4,5-b]pyridin-2-yl)ethyl]-2-fluoro-4-methyl-3-oxo-4-aza-5α-androst-1-en-17β-carboxamide | 494.2921 |
| 3 | | N-[1-(3H-imidazo[4,5-b]pyridin-2-yl)cyclopropyl]-2-fluoro-4-methyl-3-oxo-4-aza-5α-androst-1-en-17β-carboxamide | 506.2928 |

TABLE 1-continued

| Ex. | NHR[1] | Name | Mass spectrum Measured [M + H] |
|---|---|---|---|
| 4 | 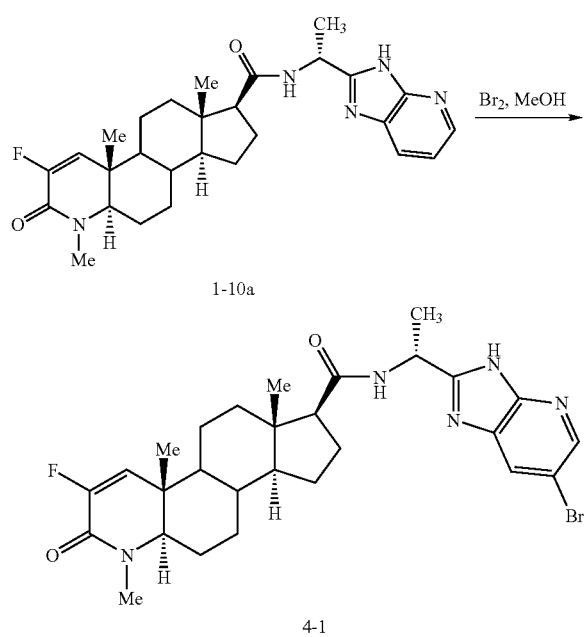 | N-[1(R)-(3H-imidazo[4,5-b]-(5-bromopyridin)-2-yl)ethyl]-2-fluoro-4-methyl-3-oxo-4-aza-5α-androst-1-en-17β-carboxamide | 572.3 |

EXAMPLE 4

Step A: N-[1(R)-(3H-imidazo[4,5-b]-(5-bromopyridin)-2-yl)ethyl]-2-fluoro-4-methyl-3-oxo-4-zaza-5α-androst-1-en-17β-carboxamide (4-1)

To a solution of 1-10a (0.5 g, 1/01 mmol.) in 3 mL of methanol at 0° C. was added NaHCO₃ (240 mg) and bromine (63 uL). After 1 hour, the mixture was diluted with ethyl acetate, and washed with saturated aqueous NaHCO₃ and brine, then dried over MgSO₄ and concentrated. The residue was chromatographed on silica gel (hexanes to EtOAc/hexanes) and the eluent fractions allowed to stand and concentrate under ambient conditions for 72 hours to produce colorless crystals of the product. The crystals were collected by filtration and allowed to air dry for 24 hours. MS M+H found 572.3.

The structure of compound was determined by single crystal X-ray crystallography on the collected crystals. The crystals obtained are orthorhombic with space group $P2_12_12_1$ and cell constants of a=7.2975(12), b=18.841(3), c=19.584(3) Å, with V=2692.7(8) Å$^3$, and Z=4. The calculated density is 1.457 g cm$^{-3}$. The formula of the asymmetric unit in the crystal structure is $C_{28}H_{35}BrFN_5O_2$, $H_2O$; one organic moiety and a water molecule of solvation.

All diffraction measurements were made using monochromatized Mo $K_\alpha$ radiation (λ=0.71073 Å) on a CCD area-detector equipped diffractometer, at T=100 K, to a θ limit of 28.28°. There are 6564 unique reflections out of 32153 measured with 4947 observed at the I≧2σ(I) level. The structure was solved by direct methods and refined using full-matrix least-squares on F$^2$ using 347 parameters and all unique reflections. The refinement converged with agreement statistics of R=0.031, wR=0.057, S=0.94, $(\Delta/\sigma)_{max}$≦0.01.

EXAMPLE 5

Pharmaceutical Composition

As a specific embodiment of this invention, 100 mg of N-[1-(3H-imidazo[4,5-b]pyridin-2-yl)cyclopropyl]-2-fluoro-4-methyl-3-oxo-4-aza-5α-androst-1-en-17β-carboxamide, is formulated with sufficient finely divided lactose to provide a total amount of 580 to 590 mg to fill a size 0, hard gelatin capsule.

While the foregoing specification teaches the principles of the present invention, with examples provided for the purpose of illustration, it is understood that the practice of the invention encompasses all of the usual variations, adoptions, or modifications, as being within the scope of the following claims and their equivalents.

ASSAYS

In Vitro and In Vivo Assays for SARM Activity Identification of Compounds

The compounds exemplified in the present application exhibited favorable activity in all of the following assays.

Hydroxylapatite-Based Radioligand Displacement Assay of Compound Affinity for Endogenously Expressed AR Materials:
  Binding Buffer: TEGM (10 mM Tris-HCl, 1 mM EDTA, 10% glycerol, 1 mM beta-mecaptoethanol, 10 mM Sodium Molybdate, pH 7.2)
  50% HAP Slurry: Calbiochem Hydroxylapatite, Fast Flow, in 10 mM Tris, pH 8.0 and 1 mM EDTA.
  Wash Buffer: 40 mM Tris, pH7.5, 100 mM KCl, 1 mM EDTA and 1 mM EGTA.
  95% EtOH
  Methyltrienolone, [17α-methyl-$^3$H], (R1881*); NEN NET590
  Methyltrienolone (R1881), NEN NLP005 (dissolve in 95% EtOH)
  Dihydrotestosterone (DHT) [1,2,4,5,6,7-$^3$H(N)] NEN NET453

Hydroxylapatite Fast Flow; Calbiochem Cat#391947
Molybdate=Molybdic Acid (Sigma, M1651)

MDA-MB-453 Cell Culture Media:

| RPMI 1640 (Gibco 11835-055) w/23.8 mM NaHCO₃, 2 mM L-glutamine in 500 mL of complete media | Final conc. |
|---|---|
| 10 mL (1M Hepes) | 20 mM |
| 5 mL (200 mM L-glu) | 4 mM |
| 0.5 mL (10 mg/mL human insulin) in 0.01 N HCl Calbiochem#407694-S) | 10 µg/mL |
| 50 mL FBS (Sigma F2442) | 10% |
| 1 mL (10 mg/mL Gentamicin Gibco#15710-072) | 20 µg/mL |

Cell Passaging

Cells (Hall R. E., et al., *European Journal of Cancer*, 30A: 484-490 (1994)) are rinsed twice in PBS, phenol red-free Trypsin-EDTA is diluted in the same PBS 1:10. The cell layers are rinsed with 1× Trypsin, extra Trypsin is poured out, and the cell layers are incubated at 37° C. for ~2 min. The flask is tapped and checked for signs of cell detachment. Once the cells begin to slide off the flask, the complete media is added to kill the trypsin. The cells are counted at this point, then diluted to the appropriate concentration and split into flasks or dishes for further culturing (Usually 1:3 to 1:6 dilution).

Preparation of MDA-MB-453 Cell Lysate

When the MDA cells are 70 to 85% confluent, they are detached as described above, and collected by centrifuging at 1000 g for 10 minutes at 4° C. The cell pellet is washed twice with TEGM (10 mM Tris-HCl, 1 mM EDTA, 10% glycerol, 1 mM beta-mercaptoethanol, 10 mM Sodium Molybdate, pH 7.2). After the final wash, the cells are resuspended in TEGM at a concentration of $10^7$ cells/mL. The cell suspension is snap frozen in liquid nitrogen or ethanol/dry ice bath and transferred to −80° C. freezer on dry ice. Before setting up the binding assay, the frozen samples are left on ice-water to just thaw (~1 hr). Then the samples are centrifuged at 12,500 g to 20,000 g for 30 min at 4° C. The supernatant is used to set-up assay right away. If using 50 µL of supernatant, the test compound can be prepared in 50 µL of the TEGM buffer.

Procedure for Multiple Compound Screening

1×TEGM buffer is prepared, and the isotope-containing assay mixture is prepared in the following order: EtOH (2% final concentration in reaction), ³H-R1881 or ³H-DHT (0.5 nM final Conc. in reaction) and 1×TEGM. [eg. For 100 samples, 200 µL (100×2) of EtOH+4.25 µL of 1:10 ³H-R1881 stock+2300 µL (100×23) 1×TEGM]. The compound is serially diluted, e.g., if starting final conc. is 1 µM, and the compound is in 25 µL of solution, for duplicate samples, 75 µL of 4×1 µM solution is made and 3 µL of 100 µM is added to 72 µL of buffer, and 1:5 serial dilution.

25 µL of ³H-R1881 trace and 25 µL compound solution are first mixed together, followed by addition of 50 µL receptor solution. The reaction is gently mixed, spun briefly at about 200 rpm and incubated at 4° C. overnight. 100 µL of 50% HAP slurry is prepared and added to the incubated reaction which is then vortexed and incubated on ice for 5 to 10 minutes. The reaction mixture is vortexed twice more to resuspend HAP while incubating reaction. The samples in 96-well format are then washed in wash buffer using The FilterMate™ Universal Harvester plate washer (Packard).

The washing process transfers HAP pellet containing ligand-bound expressed receptor to Unifilter-96 GF/B filter plate (Packard). The HAP pellet on the filter plate is incubated with 50 µL of MICROSCINT (Packard) scintillint for 30 minutes before being counted on the TopCount microscintillation counter (Packard). $IC_{50}$s are calculated using R1881 as a reference.

Unexpectedly, the compounds, Examples 1-4, found in Table 1, were tested in the above assay and found to have an $IC_{50}$ value of 0.050 micromolar or less.

Mammalian Two-Hybrid Assay for the Ligand-Induced Interaction of N-Terminus and C-Terminus Domains of the Androgen Receptor (Agonist Mode; VIRCON)

This assay assesses the ability of AR agonists to induce the interaction between the N-terminal domain (NTD) and C-terminal domain (CTD) of rhAR that reflects the in vivo virilizing potential mediated by activated androgen receptors. The interaction of NTD and CTD of rhAR is quantified as ligand induced association between a Gal4 DBD-rhARCTD fusion protein and a VP16-rhARNTD fusion protein as a mammalian two-hybrid assay in CV-1 monkey kidney cells.

The day before transfection, CV-1 cells are trypsinized and counted, and then plated at 20,000 cells/well in 96-well plates or larger plates (scaled up accordingly) in DMEM+10% FCS. The next morning, CV-1 cells are cotransfected with pCBB1 (Gal4 DBD-rhARLBD fusion construct expressed under the SV40 early promoter), pCBB2 (VP16-rhAR NTD fusion construct expressed under the SV40 early promoter) and pFR (Gal4 responsive luciferase reporter, Promega) using LIPOFECTAMINE PLUS reagent (GIBCO-BRL) following the procedure recommended by the vendor. Briefly, DNA admixture of 0.05 µg pCBB1, 0.05 µg pCBB2 and 0.1 µg of pFR is mixed in 3.4 µL OPTI-MEM (GIBCO-BRL) mixed with "PLUS Reagent" (1.6 µL, GIBCO-BRL) and incubated at room temperature (RT) for 15 min to form the pre-complexed DNA.

For each well, 0.4 µL LIPOFECTAMINE Reagent (GIBCO-BRL) is diluted into 4.6 µL OPTI-MEM in a second tube and mixed to form the diluted LIPOFECTAMINE Reagent. The pre-complexed DNA (above) and the diluted LIPOFECTAMINE Reagent (above) are combined, mixed and incubated for 15 minutes at room temperature. The medium on the cells is replaced with 40 µL/well OPTI-MEM, and 10 µL DNA-lipid complexes are added to each well. The complexes are mixed into the medium gently and incubated at 37° C. at 5% $CO_2$ for 5 hours. Following incubation, 200 µL/well D-MEM and 13% charcoal-stripped FCS are added, followed by incubation at 37° C. at 5% $CO_2$. After 24 hours, the test compounds are added at the desired concentration(s) (1 nM-10 µM). Forty eight hours later, luciferase activity is measured using LUC-Screen system (TROPIX) following the manufacturer's protocol. The assay is conducted directly in the wells by sequential addition of 50 µL each of assay solution 1 followed by assay solution 2. After incubation for 40 minutes at room temperature, luminescence is directly measured with 2-5 second integration.

Activity of test compounds is calculated as the $E_{max}$ relative to the activity obtained with R1881. The exemplified tissue-selective androgen receptor modulators of the present invention display weak or no agonist activity in this assay with less than 50% agonist activity.

See He B. Kemppainen J A, Voegel J J, Gronemeyer H, Wilson E M, "Activation function in the human androgen receptor ligand binding domain mediates inter-domain communication with the NH(2)-terminal domain," *J. Biol. Chem.* 274: 37219-37225 (1999).

Trans-Activation Modulation of Androgen Receptor (TAMAR)

This assay assesses the ability of test compounds to control transcription from the MMTV-LUC reporter gene in MDA-MB-453 cells, a human breast cancer cell line that naturally expresses the human AR. The assay measures induction of a modified MMTV LTR/promoter linked to the LUC reporter gene.

20,000 to 30,000 cells/well are plated in a white, clear-bottom 96-well plate in "Exponential Growth Medium" which consists of phenol red-free RPMI 1640 containing 10% FBS, 4 mM L-glutamine, 20 mM HEPES, 10 ug/mL human insulin, and 20 ug/mL gentamicin. Incubator conditions are 37° C. and 5% $CO_2$. The transfection is done in batch mode. The cells are trypsinized and counted to the right cell number in the proper amount of fresh media, and then gently mixed with the Fugene/DNA cocktail mix and plated onto the 96-well plate. All the wells receive 200 Tl of medium+lipid/DNA complex and are then incubated at 37° C. overnight. The transfection cocktail consists of serum-free Optimem, Fugene6 reagent and DNA. The manufacturer's (Roche Biochemical) protocol for cocktail setup is followed. The lipid (Tl) to DNA (Tg) ratio is approximately 3:2 and the incubation time is 20 minutes at room temperature. Sixteen to 24 hrs after transfection, the cells are treated with test compounds such that the final DMSO (vehicle) concentration is <3%. The cells are exposed to the test compounds for 48 hours. After 48 hours, the cells are lysed by a Promega cell culture lysis buffer for 30-60 minutes and then the luciferase activity in the extracts is assayed in the 96-well format luminometer.

Activity of test compounds is calculated as the $E_{max}$ relative to the activity obtained with 100 nM R1881.

See R. E. Hall, et al., "MDA-MB-453, an androgen-responsive human breast carcinoma cell line with high androgen receptor expression," *Eur. J. Cancer*, 30A: 484-490 (1994) and R. E. Hall, et al., "Regulation of androgen receptor gene expression by steroids and retinoic acid in human breast-cancer cells," *Int. J. Cancer.*, 52: 778-784 (1992).

Activity of test compounds is calculated as the $E_{max}$ relative to the activity obtained with R1881. The exemplified tissue-selective androgen receptor modulators of the present invention display partial agonist activity in this assay with greater that 10% and less than 100% agonist activity.

In Vivo Prostate Assay

Male Sprague-Dawley rats aged 9-10 weeks, the earliest age of sexual maturity, are used in prevention mode. The goal is to measure the degree to which androgen-like compounds delay the rapid deterioration (~–85%) of the ventral prostate gland and seminal vesicles that occurs during a seven day period after removal of the testes (orchiectomy [ORX]).

Rats are orchiectomized (ORX). Each rat is weighed, then anesthetized by isoflurane gas that is maintained to effect. A 1.5 cm anteroposterior incision is made in the scrotum. The right testicle is exteriorized. The spermatic artery and vas deferens are ligated with 4.0 silk 0.5 cm proximal to the testicle. The testicle is freed by one cut of a small surgical scissors distal to the ligation site. The tissue stump is returned to the scrotum. The same is repeated for the left testicle. When both stumps are returned to the scrotum, the scrotum and overlying skin are sutured closed with 4.0 silk. For Sham-ORX, all procedures excepting ligation and scissors cutting are completed. The rats fully recover consciousness and full mobility within 10-15 minutes.

A dose of test compound is administered subcutaneously or orally to the rat immediately after the surgical incision is sutured. Treatment continues for an additional six consecutive days.

Necropsy and Endpoints

The rat is first weighed, then anesthetized in a $CO_2$ chamber until near death. Approximately 5 ml whole blood is obtained by cardiac puncture. The rat is then examined for certain signs of death and completeness of ORX. Next, the ventral portion of the prostate gland is located and blunt dissected free in a highly stylized fashion. The ventral prostate is blotted dry for 3-5 seconds and then weighed (VPW). Finally, the seminal vesicle is located and dissected free. The ventral seminal vesicle is blotted dry for 3-5 seconds and then weighed (SVWT).

Primary data for this assay are the weights of the ventral prostate and seminal vesicle. Secondary data include serum LH (luteinizing hormone) and FSH (follicle stimulating hormone), and possible serum markers of bone formation and virilization. Data are analyzed by ANOVA plus Fisher PLSD post-hoc test to identify intergroup differences. The extent to which test compounds inhibit ORX-induced loss of VPW and SVWT is assessed.

In Vivo Bone Formation Assay:

Female Sprague-Dawley rats aged 7-10 months are used in treatment mode to simulate adult human females. The rats have been ovariectomized (OVX) 75-180 days previously, to cause bone loss and simulate estrogen deficient, osteopenic adult human females. Pre-treatment with a low dose of a powerful anti-resorptive, alendronate (0.0028 mpk SC, 2×/wk) is begun on Day 0. On Day 15, treatment with test compound is started. Test compound treatment occurs on Days 15-31 with necropsy on Day 32. The goal is to measure the extent to which androgen-like compounds increase the amount of bone formation, shown by increased fluorochrome labeling, at the periosteal surface.

In a typical assay, nine groups of seven rats each are studied.

On Days 19 and 29 (fifth and fifteenth days of treatment), a single subcutaneous injection of calcein (8 mg/kg) is given to each rat.

Necropsy and Endpoints

The rat is first weighed, then anesthetized in a $CO_2$ chamber until near death. Approximately 5 mL whole blood is obtained by cardiac puncture. The rat is then examined for certain signs of death and completeness of OVX. First, the uterus is located, blunt dissected free in a highly stylized fashion, blotted dry for 3-5 seconds and then weighed (UW). The uterus is placed in 10% neutral-buffered formalin. Next, the right leg is disarticulated at the hip. The femur and tibia are separated at the knee, substantially defleshed, and then placed in 70% ethanol.

A 1-cm segment of the central right femur, with the femoral proximal-distal midpoint ats center, is placed in a scintillation vial and dehydrated and defatted in graded alcohols and acetone, then introduced to solutions with increasing concentrations of methyl methacrylate. It is embedded in a mixture of 90% methyl methacrylate: 10% dibutyl phthalate that is allowed to polymerize over a 48-72 hours period. The bottle is cracked and the plastic block is trimmed into a shape that conveniently fits the vice-like specimen holder of a Leica 1600 Saw Microtome, with the long axis of the bone prepared for cross-sectioning. Three cross-sections of 85 µm thickness are prepared and mounted on glass slides. One section from each rat that approximates the midpoint of the bone is selected and blind-coded. The periosteal surface of each section is assessed for total periosteal surface, single fluorochrome label, double fluorochrome label, and interlabel distance.

Primary data for this assay are the percentage of periosteal surface bearing double label and the mineral apposition rate (interlabel distance(μm)/10d), semi-independent markers of bone formation. Secondary data include uterus weight and histologic features. Tertiary endpoints can include serum markers of bone formation and virilization. Data are analyzed by ANOVA plus Fisher PLSD post-hoc test to identify inter-group differences. The extent to which test compounds increase bone formation endpoint are assessed.

What is claimed is:

1. A compound of structural formula I:

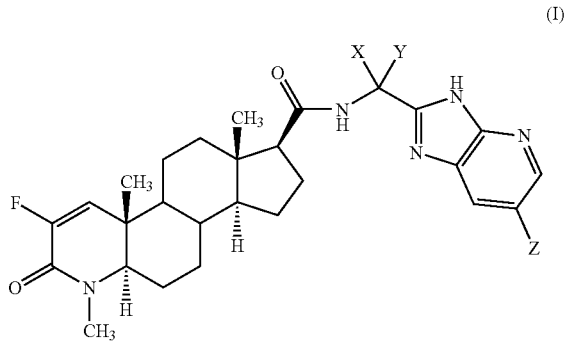

a pharmaceutically acceptable salt or a stereoisomer thereof, wherein:

X and Y are each independently chosen from hydrogen, halogen, hydroxy, and $C_{1-3}$ alkyl, wherein said alkyl is optionally substituted with one to seven fluorine atoms, provided that when X is methyl than Y is other than methyl; or X and Y, together with the carbon atom to which they are attached, can optionally form a $C_{3-6}$cycloalkyl group; and Z is chosen from hydrogen, carbonyl($C_{1-3}$ alkyl), hydroxy, $C_{1-4}$ alkoxy, halogen, hydroxymethyl, $(C_{0-6}$ alkyl$)_2$ amino, and $C_{1-3}$ alkyl, wherein said alkoxy and alkyl are each optionally substituted with one to seven fluorine atoms; and provided that when X is hydrogen, Y is other than hydrogen.

2. The compound of claim 1, wherein X is methyl and Y is selected from hydrogen and $C_{1-3}$ alkyl; or X and Y, together with the carbon atom to which they are attached, can optionally form a cyclopropyl group.

3. The compound of claim 2, wherein Z is chosen from hydrogen, and halogen.

4. The compound of claim 1, selected from:

N-[1(R)-(3H-imidazo[4,5-b]pyridin-2-yl)ethyl]-2-fluoro-4-methyl-3-oxo-4-aza-5α-androst-1-en-17β-carboxamide;

N-[1(S)-(3H-imidazo[4,5-b]pyridin-2-yl)ethyl]-2-fluoro-4-methyl-3-oxo-4-aza-5α-androst-1-en-17β-carboxamide;

N-[1-(3H-imidazo[4,5-b]pyridin-2-yl)cyclopropyl]-2-fluoro-4-methyl-3-oxo-4-aza-5α-androst-1-en-17β-carboxamide;

N-[1(R)-(3H-imidazo[4,5-b]-(5-bromopyridin)-2-yl)ethyl]-2-fluoro-4-methyl-3-oxo-4-aza-5α-androst-1-en-17β-carboxamide; and pharmaceutically acceptable salts and stereoisomers thereof.

5. A pharmaceutical composition comprising a compound of any one of claims 1-4 or a pharmaceutically acceptable salt or stereoisomer thereof and a pharmaceutically acceptable carrier.

6. A process for making a pharmaceutical composition comprising combining a compound according to any one of claims 1 to 4 or a pharmaceutically acceptable salt or stereoisomer thereof and a pharmaceutically acceptable carrier.

* * * * *